United States Patent [19]

Maraganore et al.

[11] Patent Number: 5,256,559
[45] Date of Patent: Oct. 26, 1993

[54] METHODS AND COMPOSITIONS FOR INHIBITING PLATELET AGGREGATION

[75] Inventors: John M. Maraganore, Tewksbury, Mass.; Joseph A. Jakubowski, Indianapolis, Ind.

[73] Assignees: Biogen, Inc., Cambridge; Trustees of Boston University, Boston, both of Mass.

[21] Appl. No.: 677,609

[22] Filed: Mar. 27, 1991

Related U.S. Application Data

[63] Continuation of Ser. No. 314,755, Feb. 28, 1989, abandoned, which is a continuation-in-part of Ser. No. 280,618, Dec. 5, 1988, abandoned, which is a continuation-in-part of Ser. No. 251,150, Sep. 29, 1988, abandoned, which is a continuation-in-part of Ser. No. 164,178, Mar. 4, 1988, abandoned.

[51] Int. Cl.⁵ .................. C12N 5/06; A61K 37/02; A61K 39/395; C07K 7/06
[52] U.S. Cl. .................. 435/240.2; 435/240.1; 514/12; 514/13; 514/14; 514/15; 514/16; 424/85.8; 530/324; 530/325; 530/326; 530/327; 530/328
[58] Field of Search .................. 514/12, 13, 14, 15, 514/16; 435/240.1, 240.2; 530/324, 325, 326, 327, 328; 424/85.8

[56] References Cited

U.S. PATENT DOCUMENTS

| | | | |
|---|---|---|---|
| 4,654,302 | 3/1987 | Fritz et al. | 435/70 |
| 4,668,662 | 5/1987 | Tripier | 514/12 |
| 4,683,291 | 7/1987 | Zimmerman et al. | 530/324 |
| 4,702,908 | 10/1987 | Thorbecke et al. | 424/88 |
| 4,745,177 | 5/1988 | Fritz et al. | 530/324 |
| 4,767,742 | 8/1988 | Dodt et al. | 514/12 |
| 4,791,100 | 12/1988 | Kramer et al. | 514/12 |

FOREIGN PATENT DOCUMENTS

| | | |
|---|---|---|
| 0158564 | 10/1985 | European Pat. Off. |
| 0168342 | 1/1986 | European Pat. Off. |
| 0171024 | 2/1986 | European Pat. Off. |
| 0193175 | 9/1986 | European Pat. Off. |
| 0200655 | 11/1986 | European Pat. Off. |
| 0225633 | 6/1987 | European Pat. Off. |
| 0252854 | 1/1988 | European Pat. Off. |
| 0276014 | 7/1988 | European Pat. Off. |
| 03517 | 6/1986 | PCT Int'l Appl. |

OTHER PUBLICATIONS

Mao et al., Analytical Biochemistry 161, pp. 514–518 (Mar. 1987).
Kostenansky et al., J. Med. Chem. 30, pp. 1688–1691 (Sep. 1987).
Bajusz et al., Chem. Abstr. 103, No. 31952m (1985).
Windholz et al., The Merck Index, No. 7777, pp. 1133–1134 (1983).
Rudinger, Peptide Hormones, Parsons (ad.), U. Park Press, Baltimore, pp. 1–7 (1976).
Kostenansky et al., Febb Lett. 211 pp. 10–16 (Jan. 1987).
Bajusz et al., Peptides, Proceedings of the 18th European Peptide Symposium, Sweden, pp. 473–476 (1984).
Chang. FEBs 1044, vol. 104, No. 2, pp. 307–313 (1983).
Fenton, Annals. New York Academy of Science, vol. 370, pp. 468–95 (1981).

(List continued on next page.)

Primary Examiner—Y. Christina Chan
Attorney, Agent, or Firm—James F. Haley, Jr.; Andrew S. Marks; Margaret A. Pierri

[57] ABSTRACT

This invention relates to anticoagulant and platelet inhibitory compositions, combinations and methods characterized by biologically active peptides which display the anticoagulant and platelet inhibitory activities of hirudin, or analogs thereof, for therapeutic and prophylactic purposes. The methods, compositions and combinations of this invention are advantageously useful for decreasing or preventing platelet aggregation and platelet activation in a patient or a biological sample. These methods, compositions and combinations are particularly useful in patients for whom standard heparin therapy is contraindicated due to a history of heparin-induced thrombocytopenia or an antithrombin III deficiency. This invention also relates to methods, compositions and combinations for treating extracorporeal blood and for increasing platelet storage life.

16 Claims, 8 Drawing Sheets

OTHER PUBLICATIONS

Goodman and Gilman's The Pharmacological Basis of Therapeutics, 7th Sd., Macmillan Publishing Company, New York pp. 1336-1359 (1985).

The Merck Manual of Diagnosis and Therapy, 15th Ed., Berkow (Editor), Merck Sharp and Dohme Research Lab., New Jersey, pp. 568-569, 654-655 (1987).

Jakubowski et al., Blood, vol. 75, No. 2, pp. 399-405 Jan. 15, 1990.

Maraganore et al., The Journal of Biological Chemistry, vol. 264, No. 15, pp. 8692-8698 (May 1989).

I. P. Baskova et al., "Comparative Study of Hirudin and Pseudohirudin", Biochemistry (Eng. Trans. Biokhimiya), 45, pp. 348-351 (1980).

C. Bergman et al., "Chemical Synthesis and Expression of a Gene Coding for Hirudin, the Thrombin-Specific Inhibitor from the Leech Hirudo medicinalis", *Biol. Chem. Hoppe-Seyler*, 367, pp. 731-740 (1968).

A. P. Bode et al., "Preservation of In Vitro Function of Platelets Stored in the Presence of Inhibitors of Platelet Activation and a Specific Inhibitor of Thrombin", *J. Lab. Clin. Med.*, 111, pp. 118-124 (1988).

J. Dodt et al., "Expression, Secretion and Processing of Hirudin in *E. coli* Using the Alkaline Phosphatase Signal Sequence", *FEBS Lett.*, 202, pp. 373-377 (1986).

R. P. Harvey et al., "Cloning and Expression of a CDNA, Coding for the Anticoagulant Hirudin from the Bloodsucking Leech, *Hirudo medicinalis*", *Proc. Natl. Acad. Sci. USA*, 83, pp. 1084-1088 (1986).

A. Hoffmann et al., "Inhibition of the Thrombin-Platelet Reaction by Hirudin", *Haemostasis* 14, pp. 164-69 (1984).

M. Jandrot-Perrus et al., "Cross-Linking of a α and γ-Thrombin to Distinct Binding Sites on Human Platelets", *Eur. J. Biochem.*, 174, pp. 359-67 (1988).

C. L. Knupp, "Effect of Thrombin Inhibitors on Thrombin-Induced Platelet Release and Aggregation", Thromb. Res., 49, pp. 23-36 (1988).

M. J. P. Pilat and M. S. Doscher "Molecular Analysis of the Interaction of Hirudin and Alpha-Thrombin", Fed. Proc. 45, p. 1494 (1986).

D. S. Reinhold et al., "Hirudin Insensitive Thrombin-Stimulated Platelet Release", *Thromb. Res.*, 37, pp. 513-27 (1985).

S. W. Tam et al., "Dissociation of Thrombin from Platelets by Hirudin", *J. Biol. Chem.*, 254, pp. 8723-25 (1979).

| Peptide | Position in Hirudin Sequence | Sequence | MCT*₅₀ |
|---|---|---|---|
| Hirudin53-64 | 53 - 64 | H - N G D F E E I P E E Y L - OH | 0.77 |
| Hirudin57-64 | 57 - 64 | H - E E I P E E Y L - OH | >50 |
| des (Tyr-Leu) Hirudin53-62 | 53 - 62 | H - N G D F E E I P E E - OH | >50 |
| Tyr63-O-Sulfate Hirudin53-64 | 53 - 64 | H - N G D F E E I P E E Y L - OH, OSO₃⁻H⁺ | 0.08 |
| Control | 64 - 45 | H - L Y E E P I E E F D G N N H S E P N P T - OH | >50 |

* MCT₅₀ is defined in nmoles peptide/125 μl of diluted plasma

FIG. 2

A.
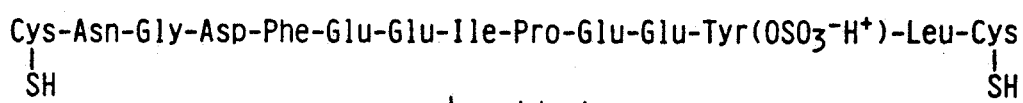
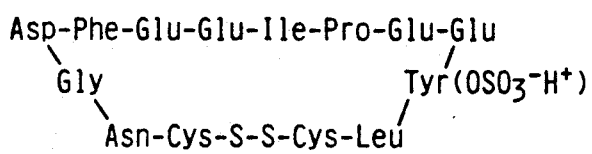
Hirulog-1
B.
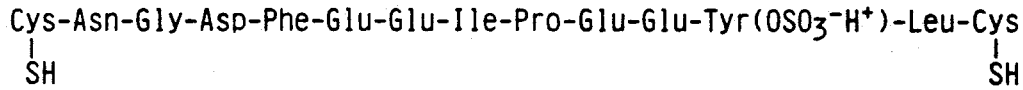
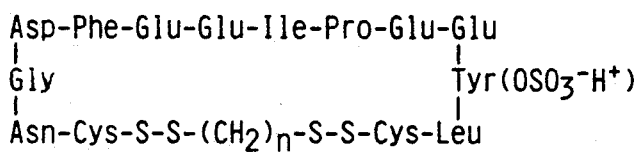
Hirulog-2
C.
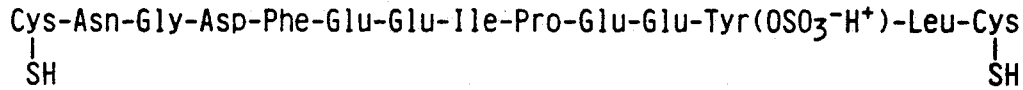
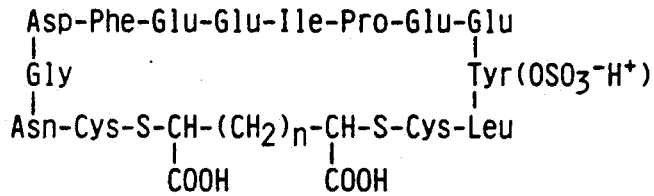
Hirulog-3
FIG. 3

A.
Lys-Asn-Gly-Asp-Phe-Glu-Glu-Ile-Pro-Glu-Glu-Tyr-(OSO₃⁻H⁺)-Leu-Lys

↓ imidate

Hirulog-4

```
        Asp-Phe-Glu-Glu-Ile-Pro-Glu-Glu-
        |                              |
        Gly              O             Tyr-(OSO₃⁻H⁺)
        |        H       ‖             |
        Asn-Lys-N-C-(CH₂)ₙ-C-N-Lys-Leu
                 ‖         H
                 O
```

FIG.4

A.
Asn-Gly-Asp-Phe-Glu-Glu-Ala(Cl)-Pro-Glu-Glu-Tyr-(OSO₃⁻H⁺)-Leu

↓

Hirulog-5

```
Asn-Gly-Asp-Phe-Glu-Glu-Ala
                      /    \
                     O      Pro
                     |      |
                     C=O    Glu
                     \    /
              Leu-(OSO₃⁻H⁺)Tyr-Glu
```

B.
Asn-Gly-Asp-Phe-Glu-Glu-Ala(Cl)-Pro-Glu-Ser-Tyr(OSO₃⁻H⁺)-Leu

↓

Hirulog-6

```
Asn-Gly-Asp-Phe-Glu-Glu-Ala-Pro
                        |    |
                        O    Glu
                        \   /
              Leu-(OSO₃⁻H⁺)Tyr-Ser
```

FIG.5

Cys-Gly-Asp-Cys-Glu-Glu-Ile-Pro-Glu-Glu-Tyr(OSO₃⁻H⁺)-Leu

↓ HS-(CH₂)₂SH

```
Cys-Gly-Asp-Cys-Glu-Glu-Ile-Pro-Glu-Glu-Tyr(OSO₃⁻H⁺)-Leu
 |              |
 S              S
  \            /
   S-(CH₂)₂-S           Hirulog-7
```

FIG.6

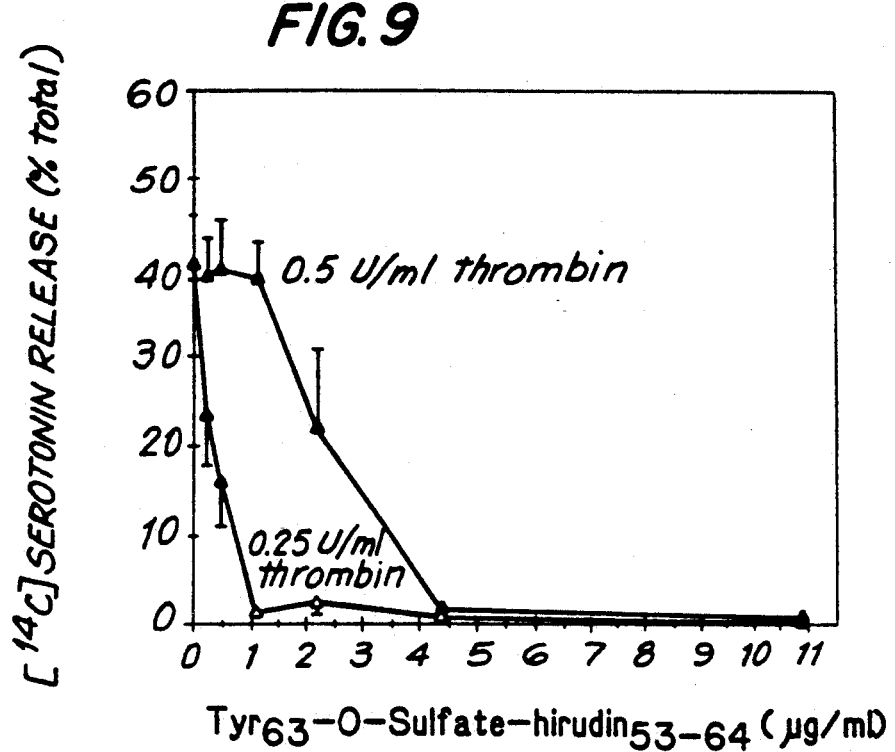
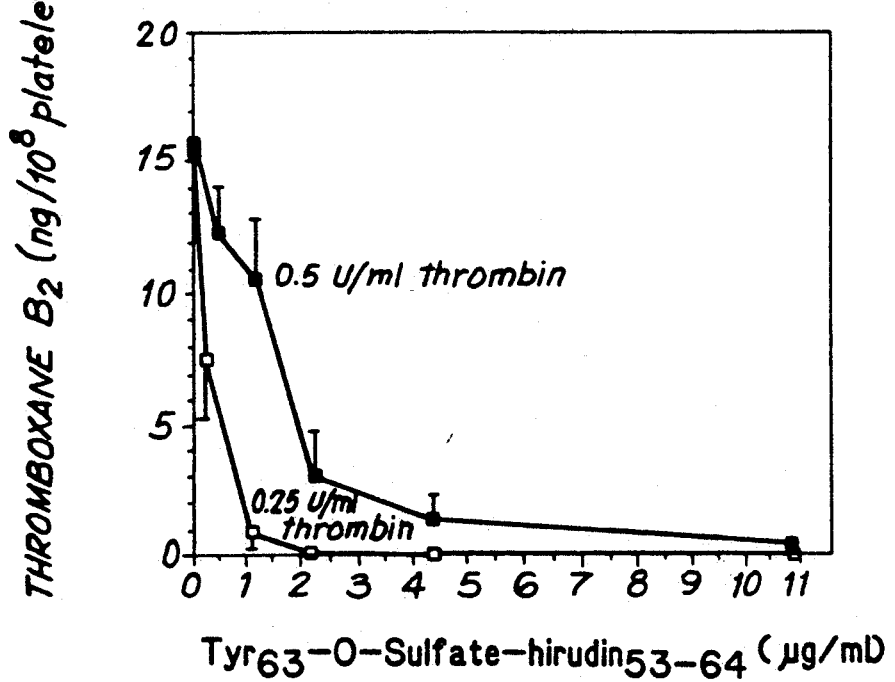

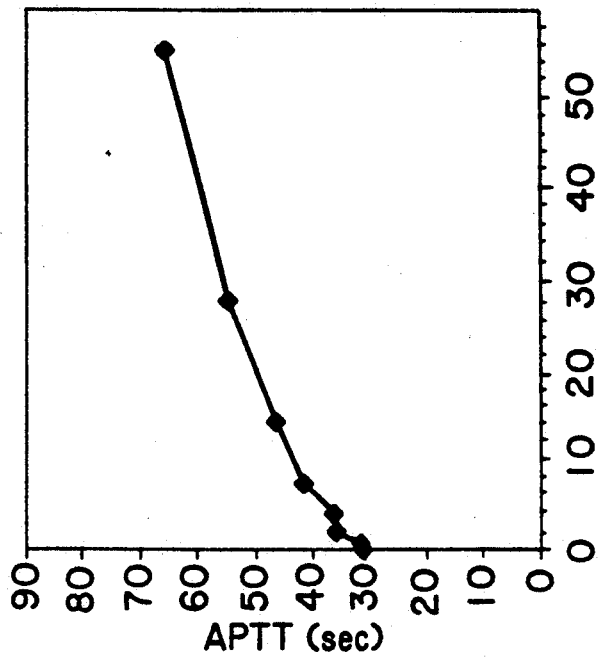
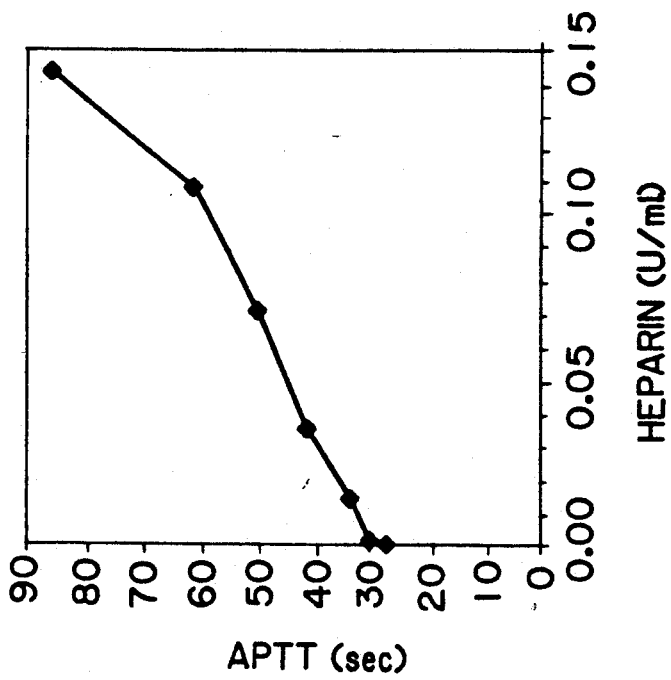

METHODS AND COMPOSITIONS FOR INHIBITING PLATELET AGGREGATION

CROSS REFERENCE TO PRIOR APPLICATIONS

This application is a continuation of application Ser. No. 314,755, filed Feb. 28, 1989, now abandoned, which is a continuation-in-part of application Ser. No. 280,618, filed Dec. 5, 1988, now abandoned, which is a continuation-in-part of application Ser. No. 251,150, filed Sept. 29, 1988, now abandoned, which is a continuation-in-part of application Ser. No. 164,178, filed Mar. 4, 1988, now abandoned.

TECHNICAL FIELD OF INVENTION

This invention relates to anticoagulant and platelet inhibitory compositions, combinations and methods characterized by biologically active peptides which display the anticoagulant and platelet inhibitory activities of hirudin, or analogs thereof, for therapeutic and prophylactic purposes. The methods, compositions and combinations of this invention are advantageously useful for decreasing or preventing platelet aggregation and platelet activation in a patient or a biological sample. These methods, compositions and combinations are particularly useful in patients for whom standard heparin therapy is contraindicated, due to a history of heparin-induced thrombocytopenia or an antithrombin III deficiency. This invention also relates to methods, compositions and combinations for treating extracorporeal blood and for increasing platelet storage life.

BACKGROUND ART

Acute vascular diseases, such as myocardial infarction, stroke, pulmonary embolism, deep vein thrombosis, peripheral arterial occlusion and other blood system thromboses constitute major health risks. Such diseases are caused by either partial or total occlusion of a blood vessel by a blood clot, which consists of one or both of fibrin and aggregated platelets.

Blood platelets play an essential role in normal hemostasis. They have both a distinct hemostatic function and a thromboplastic function. Hemostasis is initiated within a few seconds following a trauma, when platelets begin to adhere to the edges of the lesion. This initial adherence of platelets may be mediated by collagen exposed at the site of blood vessel wall trauma or by newly generated thrombin. Once in contact with collagen or thrombin, platelets undergo activation (release reaction) releasing a variety of chemicals, including ADP and thromboxane $A_2$. The released ADP and thromboxane $A_2$ cause additional platelets from the issuing blood to aggregate to those already attached to the vessel wall. The newly attached platelets also undergo the release reaction and the process continues until a hemostatic platelet plug forms. In addition to releasing ADP and thromboxane $A_2$, platelets also expose platelet factor 3, which promotes the clotting cascade, ultimately resulting in thrombin generation and fibrin deposition at the site of injury. Thrombin also binds to receptors on the platelet membrane and causes further platelet aggregation and release. The ultimate result is a mixed clot composed of aggregated platelets and polymerized fibrin.

Although necessary for normal hemostasis, clot formation resulting from platelet aggregation and release reaction is also responsible for a variety of life-threatening vascular diseases, such as myocardial infarction, stroke, peripheral arterial occlusion and other blood system thromboses. In patients suffering from such diseases, platelet aggregation is an undesirable event which should be inhibited. Inhibition of platelet aggregation may also be desirable in extracorporeal treatments of blood, such as dialysis, storage of platelets in platelet concentrates and following certain surgical procedures, such as heart-lung bypass.

During dialysis treatments, platelets tend to adhere to and aggregate on the walls of the dialysis membrane. This tends to reduce the efficiency of the treatment, as well as deplete platelets from the treated blood. In the case of platelet storage, platelet concentrates often undergo "storage lesion", a degradative process by which platelets are either activated or damaged. The practical result of such lesions is decreased storage life. Thrombin, which is generated in these platelet concentrates, is responsible for this degradation [A. P. Bode and D. T. Miller, "Generation and Degradation of Fibrinopeptide A in Stored Platelet Concentrates", Vox Sang., 51, pp. 192-96 (1986)]. In vascular surgery, the inhibition of blood clotting is essential for maintaining the integrity of the blood vessel treated. If clot formation occurs too soon after such surgery, it may threaten the life of the patient.

Although the mechanism of thrombin-induced platelet activation is poorly understood, it is believed to involve two steps: 1) binding of thrombin to a receptor on the platelet surface; and 2) thrombin-catalyzed proteolysis of a platelet surface substrate. A high-affinity thrombin binding site and a moderate-affinity thrombin binding site have been identified on the platelet surface and both are believed to be of physiological relevance [J. T. Harmon and G. A. Jamieson, "The Glycocalcin Portion of Platelet Glycoprotein Ib Expresses Both High and Moderate Affinity Receptor Sites for Thrombin", J. Biol. Chem., 261, pp. 3224-3229 (1986); J. T. Harmon and G. A. Jamieson, "Platelet Activation by Thrombin in the Absence of the High-Affinity Thrombin Receptor", Biochemistry, 27, pp. 2151-2157 (1988)].

The use of chemically modified and inhibitor-treated thrombins has demonstrated that both the binding step and the proteolysis step are components of platelet activation. For example, although thrombin treated with either hirudin or dansylarginine N-(3-ethyl-1-5-pentanediyl)amide (DAPA) cannot activate platelets, only the hirudin-treated thrombin fails to bind to the platelet thrombin receptor(s) [C. L. Knupp, "Effect of Thrombin Inhibitors on Thrombin-Induced Platelet Release and Aggregation", Thombosis Res., 49, pp. 23-36 (1988)]. Nevertheless, the inhibition of thrombin binding to platelet receptors has not been demonstrated to be sufficient to block thrombin-induced platelet activation. In fact, while hirudin blocks binding of thrombin to the platelet surface, it also inhibits the amidolytic function of the enzyme P. Walsmann and F. Markwardt, "Biochemical and Pharmacological Aspects of the Thrombin Inhibitor Hirudin", Pharmazie, 36, pp. 653-660 (1981)].

Current methods for treatment and prophylaxis of thrombotic diseases involve therapeutics which act in one of two different ways. The first type of therapeutic inhibits thrombin activity or thrombin formation, thus preventing clot formation. The second category of therapeutic accelerates thrombolysis and dissolves the blood clot, thereby removing it from the blood vessel and unblocking the flow of blood [J. P. Cazenave et al., *Agents Action*, 15, Suppl., pp. 24–49 (1984)].

Heparin, a compound of the former class, has been used widely to treat conditions, such as venous thromboembolism, in which thrombin activity is responsible for the development or expansion of a thrombus. Heparin exerts its effects by activating antithrombin III, a protein which complexes with and inactivates thrombin. Because of its mode of action, heparin is useful to prevent only thrombin-induced platelet aggregation. Even in that application, however, the overall efficacy of heparin is questionable. Furthermore, heparin produces many undesirable side effects, including hemorrhaging and heparin-induced thrombocytopenia. Moreover, in patients suffering from heparin-induced thrombocytopenia, an immune-mediated thrombocytopenia that may have dire thrombotic consequences, heparin actually accelerates platelet aggregation, often with fatal consequences. In other patients, such as those having an anti-thrombin III deficiency, heparin is simply less effective. Accordingly, the need exists for alternatives to conventional heparin-based therapies.

Hirudin is a naturally occurring polypeptide which is produced by the blood sucking leech *Hirudo medicinalis*. This compound, which is produced in the salivary gland of the leech, is the most potent natural inhibitor of coagulation known. Hirudin prevents blood from coagulating by binding tightly to thrombin ($K_d \sim 2 \times 10^{-11}$M) in a 1:1 stoichiometric complex [S. R. Stone and J. Hofsteenge, "Kinetics of the Inhibition of Thrombin by Hirudin", *Biochemistry*, 25, pp. 4622–28 (1986)]. This, in turn, inhibits thrombin from catalyzing the conversion of fibrinogen to fibrin (clot).

The actual binding between hirudin and thrombin is a two-step process. Initially, hirudin binds to a "low" affinity site on the thrombin molecule ($K_d \sim 1 \times 10^{-8}$M) which is separate from the catalytic site. Following the low affinity binding, hirudin undergoes a conformational change and then binds to the "high" affinity site on thrombin. This latter site corresponds to the active site of thrombin.

Hirudin has been shown to inhibit both the binding of thrombin to platelets [P. Ganguly and W. J. Sonnichsen, "Binding of Thrombin to Human Platelets and its Possible Significance", *Br. J. Haemotol.*, 34, pp. 291–301 (1976); S. W. Tam and T. C. Detwiler, "Binding of Thrombin to Human Platelet Plasma Membrane", *Biochim. Biophys. Acta*, 543, pp. 194–201 (1978) and thrombin-induced platelet aggregation [S. W. Tam et al., "Dissociation of Thrombin From Platelets by Hirudin: Evidence for Receptor Processing", *J. Biol. Chem.*, 254, pp. 8723–25 (1979)]. Therefore, hirudin has been viewed as a potential antiplatelet agent. However, several drawbacks are associated with hirudin use, including high cost, potential antigenicity and hemorrhaging.

The isolation, purification and chemical composition of hirudin are known in the art [P. Walsmann and F. Markwardt, "Biochemical and Pharmacological Aspects of the Thrombin Inhibitor Hirudin", *Pharmazie*, 36, pp. 653–60 (1981)]. More recently, the complete amino acid sequence of the polypeptide has been elucidated [J. Dodt et al. "The Complete Covalent Structure of Hirudin: Localization of the Disulfide Bonds", *Biol. Chem. Hoppe-Seyler*, 366, pp. 379–85 (1985); S. J. T. Mao et al., "Rapid Purification and Revised Amino Terminal Sequence of Hirudin: A Specific Thrombin Inhibitor of the Blood-Sucking Leech", *Anal. Biochem*, 161, pp. 514–18 (1987); and R. P. Harvey et al., "Cloning and Expression of a cDNA Coding for the Anti-Coagulant Hirudin from the Bloodsucking Leech, *Hirudo medicinalis*", *Proc. Natl. Acad. Sci. USA*, 83, pp. 1084–88 (1986)].

At least two different isospecific forms of hirudin, HV-1 and HV-2, have been sequenced and have been shown to differ slightly in amino acid sequence [R. P. Harvey et al., supra]. Both forms of hirudin comprise a single polypeptide chain protein containing 65 amino acids in which the amino terminus primarily comprises hydrophobic amino acids and the carboxy terminus typically comprises polar amino acids. More specifically, all forms of hirudin are characterized by an N-terminal domain (residues 1–39) stabilized by three disulfide bridges in a 1–2, 3–5, and 4–6 half-cysteinyl pattern and a highly acidic C-terminal segment (residues 40–65). In addition, the C-terminal segment of hirudin is characterized by the presence of a tyrosine residue at amino acid position 63 which is sulfated.

In animal studies, hirudin, purified from leeches, has demonstrated efficacy in preventing venous thrombosis, vascular shunt occlusion and thrombin-induced disseminated intravascular coagulation. In addition, hirudin exhibits low toxicity, little or no antigenicity and a very short clearance time from circulation [F. Markwardt et al., "Pharmacological Studies on the Antithrombotic Action of irudin in Experimental Animals", *Thromb. Haemostasis*, 47, pp. 226–29 (1982)].

Despite hirudin's effectiveness, however, studies have shown that hirudin prolongs bleeding time in a dose-dependent manner, thus making the determination and administration of proper dosages critically important. Furthermore, the high cost and low supply of the naturally occurring product has prevented its widespread use.

In an effort to create a greater supply of hirudin, attempts have been made to produce the polypeptide through recombinant DNA techniques. The presence of an O-sulfated tyrosine residue on native hirudin and the inability of microorganisms to perform a similar protein modification made the prospect of recombinant production of biologically active hirudin highly speculative. The observation that desulfato-hirudins were almost as active as their sulfated counterparts [U.S. Pat. No. 4,654,302], however, led the way to the cloning and expression of hirudin in *E.coli* [European patent applications 158,564, 168,342 and 171,024] and yeast [European patent application 200,655]. Despite these advances, hirudin is still somewhat expensive to produce and it is not widely available commercially.

Recently, efforts have been made to identify peptide fragments of native hirudin which are also effective in lowering clotting time. An unsulfated 21 amino acid C-terminal fragment of hirudin, $N^\alpha$-acetylhirudin$_{45-65}$, inhibits clot formation in vitro. In addition, several other smaller, unsulfated peptides corresponding to the C-terminal 11 or 12 amino acids of hirudin (residues 55–65 and 54–65) have also demonstrated efficacy in inhibiting clot formation in vitro [J. L. Krstenansky et al., "Antithrombin Properties of C-terminus of Hirudin Using Synthetic Unsulfated $N^\alpha$-acetyl-hirudin$_{45-65}$", *FEBS Lett*, 211, pp. 10–16 (1987)]. Such peptide fragments, however, may not be fully satisfactory to dissolve blood clots in on-going therapy regimens. For example, $N^\alpha$-acetylhirudin$_{45-65}$ has a specific activity four orders of magnitude lower than native hirudin.

Accordingly, the need still exists for an effective inhibitor of both clot formation and platelet aggregation and secretion that is not characterized by the side effects associated with conventional agents and which can be produced in commercially feasible amounts.

DISCLOSURE OF THE INVENTION

The present invention solves the problems referred to above by providing compositions, combinations and methods characterized by peptides having the biological activity of native hirudin which are effective as both anticoagulants which cause an increase in blood clotting time and as antiplatelet agents which inhibit platelet aggregation and activation ("antiplatelets"). As will be appreciated from the disclosure to follow, the antiplatelet compositions, combinations and methods of the present invention are effective and safe in preventing platelet aggregation and secretion in the treatment and prophylaxis of vascular disease, in the treatment of extracorporeal blood and in the preservation of stored platelet concentrates.

Advantageously, the antiplatelet compositions, combinations and methods of this invention are particularly useful in patients for whom standard heparin therapy is contraindicated. For example, in patients with heparin-induced thrombocytopenia, the compositions of this invention anticoagulate plasma without causing platelet activation. And the small size of the hirudin peptides which characterize these compositions decreases the possibility of an adverse antigenic response in patients treated with them.

BRIEF DESCRIPTION OF THE DRAWINGS

FIG. 2 is a table which displays the covalent structures of hirudin peptides, as well as their anticoagulant activity. In this figure, the amino acids are represented by single letter codes as follows:

| Phe: | F | Leu: | L | Ile: | I | Met: | M |
| Val: | V | Ser: | S | Pro: | P | Thr: | T |
| Ala: | A | Tyr: | Y | His: | H | Gln: | Q |
| Asn: | N | Lys: | K | Asp: | D | Glu: | E |
| Cys: | C | Trp: | W | Arg: | R | Gly: | G |

FIGS. 3A-3C depict the synthesis of hirulog-1, hirulog-2 and hirulog-3, peptidomimetic analogs of heparin peptides.

FIG. 4A depicts the synthesis of hirulog-4, a peptidomimetic analog of a hirudin peptide.

FIGS. 5A and 5B depict the synthesis of hirulog-5 and hirulog-6, peptidomimetic analogs of hirudin peptides.

FIG. 6 depicts the synthesis of hirulog-7, a peptidomimetic analog of a hirudin peptide.

Figure 7:
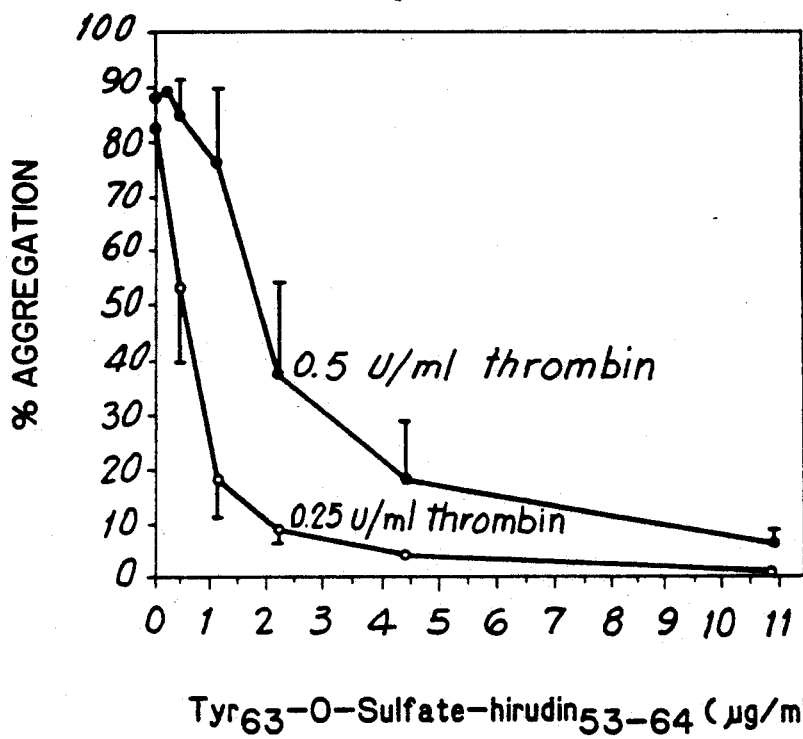

FIG. 7 depicts the effect of $Tyr_{63}$-O-sulfate hirudin$_{53-64}$ on thrombin-induced platelet aggregation.

Figure 8:
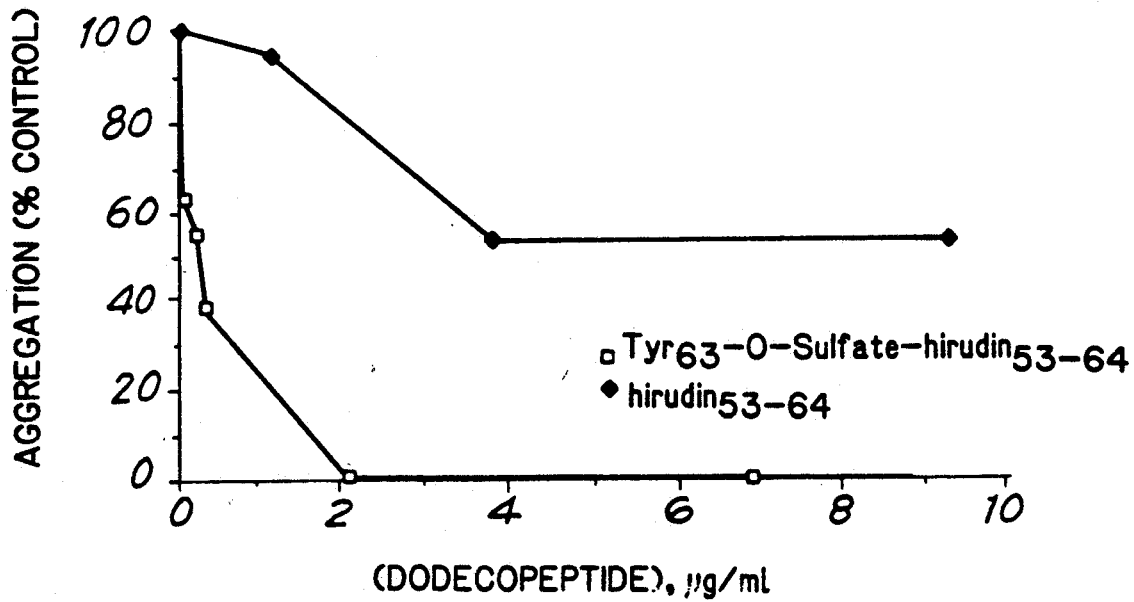

FIG. 8 depicts a comparison of the effects of $Tyr_{63}$-O-sulfate hirudin$_{53-64}$ and hirudin$_{53-64}$ on thrombin-induced platelet aggregation.

FIG. 9 depicts the effect of $Tyr_{63}$-O-sulfate hirudin$_{53-64}$ on thrombin-induced platelet release reaction.

FIG. 10 depicts the effect of $Tyr_{63}$-O-sulfate hirudin$_{53-64}$ on thrombin-induced thromboxane $A_2$ generation from platelets as measured by thromboxane $B_2$.

Figure 11A:
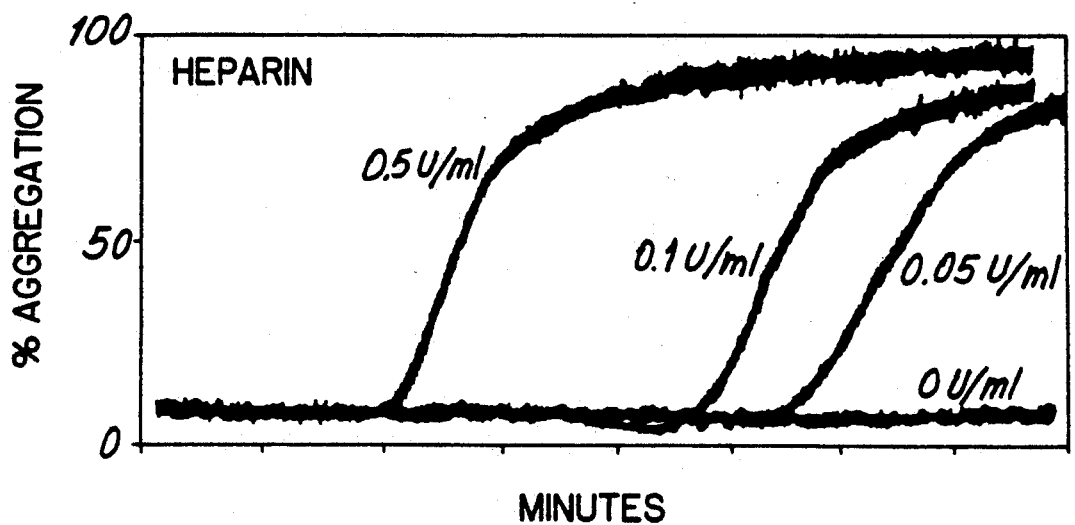
Figure 11B:
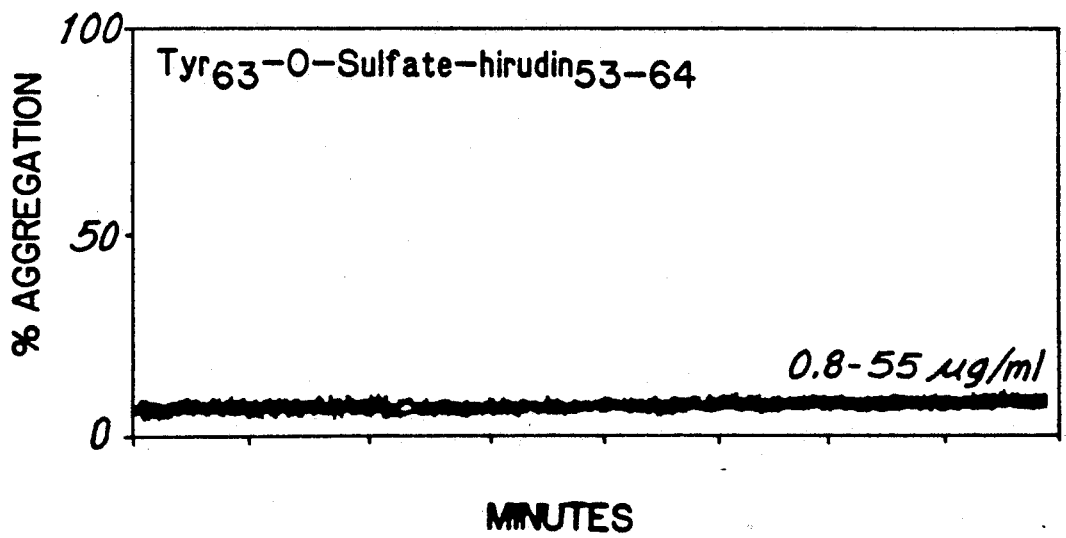

FIGS. 11A and 11B depict a comparison of the effects of heparin and $Tyr_{63}$-O-sulfate hirudin$_{53-64}$ on aggregation of platelets obtained from patients suffering from heparin-induced thrombocytopenia.

FIGS. 12A and 12B depict a comparison of the effects of heparin and $Tyr_{63}$-O-sulfate hirudin$_{53-64}$ on the activated partial thrombin times of plasma obtained from patients suffering from heparin-induced thrombocytopenia.

DESCRIPTION OF THE INVENTION

The present invention relates to pharmaceutically acceptable compositions and combinations containing hirudin peptides and methods employing them to inhibit platelet aggregation and activation in a patient, in extracorporeal blood and in stored platelets. The compositions, combinations and methods of the present invention are characterized by hirudin peptides which correspond to the amino acid sequence of the carboxyl terminal portion of hirudin and which display the anticoagulant and platelet inhibitory activities of native hirudin. Hirudin peptides are homologous to at least a portion of the carboxy terminal 26 amino acids of native hirudin. Such peptides may be derivatized at the single tyrosine residue by the addition of a negatively charged side group.

Hirudin peptides include, but are not limited to: peptides characterized by a sequence of amino acids consisting substantially of the formula: Asn-Gly-Asp-Phe-Glu-Glu-Ile-Pro-Glu-Glu-Tyr-X, and D-retro forms thereof; wherein X is selected from the group consisting of OH, Leu and Leu-Gln. Additionally, hirudin peptides include those which are characterized by a sequence of amino acids consisting substantially of the formula: Y-Phe-Glu-Glu-Ile-Pro-Glu-Glu-Tyr-Z, and D-retro forms thereof; wherein Y is selected from the group consisting of H, an amino protecting group, at least the C-terminal portion of the amino acid sequence: Val-Thr-Gly-Glu-Gly-Thr-Pro-Lys-Pro-Gln-Ser-His-Asn-Asp-Gly-Asp, and at least the C-terminal portion of the amino acid sequence: Val-Thr-Gly-Glu-Gly-Thr-Pro-Asn-Pro-Glu-Ser-His-Asn-Asn-Gly-Asp; Z is selected from the group consisting of OH, Leu and Leu-Gln; and the tyrosine residue is characterized by the presence of a negatively charged side group. In such peptides, the negatively charged side group may be selected from the group consisting of sulfate, phosphate, carboxylate, sulfonate, phosphonate, carbonate, methyl sulfonate, methyl phosphonate and variants thereof. Hirudin peptides may also include those in which Y is Asn-Gly-Asp and Z is Leu and the tyrosine residue is sulfated. In addition, hirudin peptides may be characterized by the presence of an N-acetyl group on the amino terminal amino acid.

The production of the hirudin peptides which characterize the compositions, combinations and methods of this invention may be achieved by a variety of methods known in the art. For example, the peptides may be derived from the intact hirudin molecule by proteolysis using specific endopeptidases in combination with exopeptidases, Edman degradation, or both. The intact hirudin molecule, in turn, may be purified from its natural source, *H. medicinalis*, using conventional methods. Alternatively, hirudin may be produced by known recombinant DNA techniques using cDNAs [R. P. Harvey et al., *Proc. Natl. Acad. Sci. USA*, 83, pp. 1084-88 (1986); J. Dodt et al., "Expression Secretion and Processing of Hirudin in E. coli Using the Alkaline Phosphatase Signal Sequence", *FEBS Lett.*, 202, pp. 373-77

(1986)], or a chemically synthesized gene [C. Bergmann et al., "Chemical Synthesis and Expression of a Gene Coding for Hirudin, the Thrombin-Specific Inhibitor from the Leech, *Hirudo medicinalis*", *Biol. Chem. Hoppe-Seyler*, 367, pp. 731-40 (1986)]. Also, hirudin peptides may be produced recombinantly as part of a fusion protein. Such a fusion protein may be designed so that the desired peptide may be released by appropriate enzymatic cleavage.

Preferably, hirudin peptides are produced directly, thus eliminating the need for an entire hirudin molecule as a starting material. This may be achieved by well known recombinant DNA techniques wherein only those DNA sequences which encode the desired peptides are expressed in transformed hosts.

Alternatively, hirudin peptides may be produced by conventional chemical synthesis techniques. The relatively small size of these peptides (between about 8 and 26 amino acids) advantageously allows them to be produced synthetically. Thus, they may be produced in extremely high yields and are easily purified, as compared to either native hirudin or its full length recombinant DNA counterpart. Preferably, hirudin peptides are synthesized by solid phase peptide synthesis or solution phase peptide synthesis and, optionally, digested with carboxypeptidase (to remove C-terminal amino acids) or degraded by manual Edman degradation (to remove N-terminal amino acids). Synthesis via solution phase methods advantageously allow the direct addition of derivatized amino acids onto the growing peptide chain. This obviates the need for a subsequent derivatization step to modify the tyrosine residue. Peptides produced in this way may then be purified by separation techniques widely known in the art, preferably utilizing reverse phase HPLC.

Throughout this specification and in the claims, the abbreviations employed for amino acids and their residues are used in conformity with the generally accepted rules of nomenclature and relate to a-amino acids and their residues of the L-series. However, the compositions of the present invention also include those characterized by the D-retro forms of the hirudin peptides described herein. These are produced by synthesis with D amino acids in the opposite orientation, beginning with the carboxy terminal amino acid of the L form.

Derivatization of hirudin peptides may involve the addition of a negatively charged side group onto either the free phenolic hydroxyl or the adjacent 3- or 5 position ring carbon of the single tyrosine residue. The derivatization may involve the addition of a variety of negatively charged side groups which are known in the art. Derivatization methods include, but are not limited to, sulfation, phosphorylation, and carboxylation of the tyrosine hydroxyl group, the addition of methane sulfonic acid or methane phosphonic acid onto the tyrosine hydroxy group, as well as sulfonation, phosphonation and carbonation of the tyrosine 3- or 5 position ring carbon. Techniques for performing these reactions are also well known in the art.

Most preferably, hirudin peptides are derivatized by sulfation. A preferred hirudin peptide which characterizes the compositions, combinations and methods of this invention is $Tyr_{63}$-O-sulfate $hirudin_{53-64}$, a 12 amino acid peptide, having a sulfated tyrosine residue, that is homologous to residues 53-64 of native hirudin. Another preferred peptide is 3-Sulfo-$Tyr_{63}hirudin_{53-64}$, which possesses a sulfonated tyros residue. This latter peptide may have a longer biological half-life than its sulfated counterpart.

Sulfation of hirudin peptides may be achieved either by a biological (enzymatic) or a chemical process. Preferably, a purified hirudin peptide is reacted concurrently with dicyclohexylcarbodiimide and sulfuric acid in an organic solvent. Sulfonation of the meta carbon results as a side reaction of this sulfation process.

For large-scale sulfations, the sulfation procedure is modified, so that gram quantities of the peptide are first dissolved in an organic solvent, preferably dimethylformamide, and then reacted with a dehydrating agent, preferably dicyclohexylcarbodiimide. The dehydrated tyrosine residue of the peptide is then sulfated by reaction with sulfuric acid. The reaction is complete upon formation of an insoluble dicyclohexyl urea salt. This modification results in high yields of sulfated peptide on a large scale. Advantageously, this sulfation technique may be used to sulfate the tyrosine residues of any peptide or polypeptide whether isolated and purified or present in a crude preparation. Following either sulfation reaction, the sulfated peptide may be separated from any sulfonated peptide, as well as from unreacted peptide by HPLC, DEAE chromatography, or any of several other conventional separation techniques.

Sulfation may also be achieved by reacting a hirudin peptide with sulfur trioxide-triethylamine salt in pyridine. In addition, a tyrosylsulfotransferase activity, either as a crude preparation or as a purified enzyme, may be used to sulfate the tyrosine residue [R. W. H. Lee and W. B. Huttner, "Tyrosine O Sulfated Proteins of PC-12 Pheo Chromo Cytoma Cells and Their Sulfation By a Tyrosyl Protein Sulfotransferase", *J. Biol. Chem.*, 258, pp. 11326-34 (1983). Phosphorylation or carboxylation of hirudin peptides may be achieved by reactions similar to those described above for sulfation, with the substitution of phosphoric acid or formic acid, respectively, for sulfuric acid. In those reactions, phosphonation or carbonation will occur, respectively, as a side reaction. Alternatively, enzymatic methods may be employed for carboxylation or phosphorylation of hirudin peptides.

Methyl sulfonation and methyl phosphonation of hirudin peptides may be achieved by methods well-known in the art including, but not limited to, alkylation with chlorosulfonic or chlorophosphonic acid, respectively.

The extent of the sulfation reaction may be followed spectrophotometrically. The absorbance spectra of sulfated peptides reveal a shift in maximal absorbance from approximately 275 nm to approximately 250-265 nm. Confirmation of derivatization may be obtained by desulfating the peptide with 30% trifluoroacetic acid at 60° C. for 30 minutes. This will result in an increase of maximal absorbance back to 275 nm.

The hirudin peptides useful in the compositions, combinations and methods of this invention may also be derivatized at their amino terminus by the addition of an N-acetyl group. N-acetylation may be achieved by any of a number of techniques that are known to those of skill in the art. Preferably, acetylation i achieved by using an N-acetyl amino acid derivative in the synthesis of the peptides of this invention. Alternatively, N-acetylation may be achieved by reacting the peptide with acetic anhydride. N-acetylated hirudin peptides advantageously demonstrate increased biostability as compared to their corresponding unacetylated peptide counterparts.

The platelet inhibitory potency of the hirudin peptides used in the compositions, combinations and methods of the present invention depends, in part, on their in vivo half-life. Accordingly, this invention also relates to pharmaceutical compositions, either covalent or non-covalent, comprising hirudin peptides coupled to pharmaceutically acceptable polymers which increase the biological half-life of those peptides. For example, a hirudin peptide may be coupled to an activated derivative of polyethyleneglycol (PEG) using conventional techniques. Preferably, a PEG N-succinimidyl succinate is attached to the $\alpha$-amino moiety of the peptide. Such attachment is effected by reacting the peptide with the PEG N-succinimidyl succinate reagent (SS-PEG) in an organic solvent or a buffered solution having a pH greater than about 7.0. Most preferably, about a 50-fold molar excess of SS-PEG (Avg. MW = 5,000 daltons) is reacted with a peptide in a 20 mM sodium borate buffer, pH 9.0.

Hirudin peptides are useful alone, or in compositions, combinations and methods for the treatment and prophylaxis of vascular diseases attributed to blood system thromboses. For example, hirudin peptides, as well as compositions and combinations containing them, may be used for heparin replacement for prophylactic purposes, heparin replacement in the treatment of thrombocytopenia, treatment of disseminated intravascular coagulation and treatment of vascular thrombin that may arise from any disease state. Hirudin peptides, as well as compositions and combinations containing them, may be used in the treatment or prophylaxis of vascular diseases in patients including mammals and, in particular, humans.

Hirudin peptides, or compositions containing them, may also be used to inhibit platelet aggregation in extracorporeal blood. As used in this application, the term "extracorporeal blood" includes blood removed in line from a patient, subjected to extracorporeal treatment, and returned to the patient in processes such as dialysis procedures or blood filtration or blood bypass during surgery. The term also includes blood products which are stored extracorporeally for eventual administration to a patient. Such products include whole blood, plasma or any blood fraction in which inhibition of platelet aggregation is desired. The amount or concentration of active peptide in these types of compositions will be based on the volume of blood to be treated or, more preferably, its thrombin content.

The compositions, combinations and methods of the present invention also include those characterized by peptidomimetic analogs of the hirudin peptides described herein. Peptidomimetic analogs mimic the three-dimensional structure of the active site contained in the parent peptide. The analogs inhibit thrombin hydrolysis of fibrinogen and display anticoagulant activity. For example, analogs of hirudin peptides may be either semi-peptidic or non-peptidic in nature. These peptidomimetic analogs advantageously exhibit increased shelf-life and biostability when compared to the parent compound. Moreover, the bioavailability of these peptidomimetic analogs may be greater than the corresponding peptides when administered by oral or topical routes. Furthermore, these analogs may exhibit increased antiplatelet activity. It should be understood that the peptidomimetic analogs of this invention are characterized by biological activities that are similar to those of the hirudin peptides described herein. Accordingly, these analogs may be employed in compositions, combinations and methods of this invention in the same manner as hirudin peptides.

According to a further embodiment of the present invention, pharmaceutically acceptable compositions and methods for increasing platelet storage life may further comprise other inhibitors of platelet aggregation and breakdown. These combinations include, but are not limited to metal chelaters, prostaglandins, theophylline, other small platelet inhibitory peptides, inhibitors of other platelet surface components, antibodies to platelet surface components, analogs of any of the above compounds or combinations thereof. Preferably, these additional components are citrate-phosphate dextrose, prostaglandin $PGE_1$, analogs of prostaglandin $E_1$, stable analogs of prostacyclin or teeophylline. As defined herein, the term "combination" includes a single dosage form containing at least one hirudin peptide and another inhibitor of platelet aggregation, a multiple dosage form wherein the two agents are administered separately, but concurrently, or a multiple dosage form wherein the two agents are administered separately, but sequentially.

According to another embodiment of the invention, pharmaceutically acceptable compositions and methods for inhibiting platelet aggregation in a treated patient may further comprise other platelet inhibitors such as prostaglandins, theophylline, other small platelet inhibitory peptides, cyclooxygenase inhibitors, small non-peptide platelet inhibitors, inhibitors of platelet surface components, antibodies to platelet surface components, hematopoietic factors, analogs of any of the above compounds or combinations thereof. Most preferred are aspirin, ticlopidine, dipyridamole, sulphinpyrazone, prostaglandin $E_1$, stable prostacyclin derivatives, monoclonal antibodies against glycoprotein IIb/IIIa or natural inhibitors of glycoprotein IIb/IIIa, monoclonal antibodies against glycoprotein Ib, natural inhibitors of glycoprotein Ib, erythropoietin, arg-gly-asp containing peptides or derivatives of arg-gly-asp-containing peptides.

The hirudin peptides useful in the compositions and combinations of this invention may be formulated using conventional methods to prepare pharmaceutically useful antiplatelet compositions and combinations. Such compositions preferably include at least one pharmaceutically acceptable carrier. See, e.g., *Remington's Pharmaceutioal Sciences* (E. W. Martin). In addition, the antiplatelet compositions of the present invention preferably include a pharmaceutically acceptable buffer, preferably phosphate buffered saline, together with a pharmaceutically acceptable compound for adjusting isotonic pressure, such as sodium chloride, mannitol or sorbitol. The pharmaceutically acceptable compositions and methods of this invention are characterized by pharmaceutically effective amounts of hirudin peptides—amounts effective to inhibit or reduce platelet aggregation in a biological sample for some period of time.

Such compositions are suitably adapted for oral, parenteral and topical administration, but are preferably formulated for parenteral administration. Parenteral compositions are most preferably administered in an intravenous bolus form. Compositions formulated for topical administration may, for example, be in aqueous jelly, oily suspension or emulsified ointment form. For parenteral administration, fluid unit dose forms are prepared which contain a composition of the present invention and a sterile vehicle. The hirudin peptide contained in the pharmaceutically acceptable composition may be either suspended or dissolved, depending on the nature of the vehicle and the nature of the peptide. Parenteral compositions are normally prepared by dissolving the peptide, optionally together with other components, in a vehicle and filter sterilizing before filling into a suitable vial or ampule and sealing. Preferably, adjuvants such as a local anesthetic, preservatives and buffering agents are also dissolved in the vehicle. The composition may then be frozen and lyophilized to enhance stability.

Parenteral suspensions are prepared in substantially the same manner, except the hirudin peptide is suspended in the vehicle rather than dissolved. Sterilization of the peptide and other optional components is preferably achieved by exposure to ethylene oxide before suspending in the sterile vehicle. Advantageously, a surfactant or wetting agent is included in the composition to facilitate uniform distribution of the hirudin peptide or other optional components.

Tablets and capsules for oral administration contain conventional excipients, such as binding agents, fillers, diluents, tableting agents, lubricants, disintegrants, and wetting agents. The tablet may be coated according to methods well known in the art. Suitable fillers which may be employed include cellulose, mannitol, lactose and other similar agents. Suitable disintegrants include, but are not limited to, starch, polyvinylpyrrolidone and starch derivatives, such as sodium starch glycolate. Suitable lubricants include, for example, magnesium stearate. Suitable wetting agents that are useful include sodium lauryl sulfate.

Oral liquid preparations may be in the form of aqueous or oily suspensions, solutions, emulsions, syrups or elixirs, or may be presented as a dry product for reconstitution with water or another suitable vehicle before use. Such liquid preparations may contain conventional additives. These include suspending agents; such as sorbitol, syrup, methyl cellulose, gelatin, hydroxyethylcellulose, carboxymethylcellulose, aluminum stearate gel or hydrogenated edible fats; emulsifying agents which include lecithin, sorbitan monooleate or acacia; non-aqueous vehicles, such as almond oil, fractionated coconut oil, and oily esters; and preservatives, such as methyl or propyl p-hydroxybenzoate or sorbic acid.

This invention also relates to methods for utilizing the above-described pharmaceutically acceptable compositions to decrease or prevent platelet aggregation and secretion in a patient or in a biological sample. The dosage and dose rate will depend on a variety of factors, such as the specific composition, the object of the treatment, i.e., therapy or prophylaxis, and the judgment of the treating physician. Typical daily dosage ranges for the compositions of this invention include those in which the concentration of peptide administered is between about 1 mg/ml to 1,000 mg/ml, preferably between about 25 mg/ml to 50 mg/ml. Such dosages should preferably produce in a treated patient, a final in vivo concentration of between about 0.1 to 10 mg peptide/kg of body weight, most preferably between about 0.2 to 2 mg/kg body weight. The duration of treatment will be for a time sufficient to produce the desired inhibition of platelet aggregation. Because the PEG derivatized hirudin peptides which may be used in the compositions of this invention display a longer half-life as compared to native hirudin, as well as the underivatized peptides, their dosage amounts are advantageously well below the amounts recommended above for the underivatized peptides.

A preferred embodiment of this invention relates to a method for inhibiting platelet aggregation in patients for whom heparin treatment is contraindicated. Specifically, these methods are particularly effective in patients who have suffered from or who are currently suffering from heparin-induced thrombocytopenia. Determination that a patient is or has suffered from heparin-induced thrombocytopenia may be made by patient interview, medical history, or more preferably by directly assaying the platelet content in a sample of blood during heparin therapy. Such assays, which are well-known in the art, detect heparin-induced platelet aggregation, heparin-induced [$^{14}$C] serotonin release or heparin-induced thromboxane $A_2$ release from platelets [J. C. Fratantoni et al., "Heparin Induced Thrombocytopenia: Confirmation of Diagnosis with In Vitro Methods", *Blood*, 45, pp. 395–401 (1975); J. G. Kelton et al., "Clinical Usefulness of Testing for A Heparin Dependent Platelet Aggregation Factor in Patients with Suspected Heparin Associated Thrombocytopenia", *J. Lab Clin. Med.*, 103, pp. 606–12 (1984); D. Sheridan et al., "A Diagnostic Test For Heparin Induced Thrombocytopenia", *Blood*, 67, pp. 27–30 (1986)].

According to an alternate embodiment of this invention, hirudin peptide-containing compositions may be used to increase platelet storage life. The final concentration of peptide in these compositions ranges from about 0.5 μg/ml to 1,000 μg/ml, preferably about 5 μg/ml to 100 μg/ml. According to still another embodiment, the final concentration of $PGE_1$, or theophylline in the platelet storage compositions of this invention will range between about 1 nM to 10 μM, preferably between about 100 nM to 750 nM for $PGE_1$, and between about 10 μM to 10 mM for theophylline.

In order that this invention may be more fully understood, the following examples are set forth. It should be understood that these examples are for illustrative purposes only and are not to be construed as limiting this invention in any manner.

In all of the examples of peptide syntheses described below, we carried out amino acid analysis of the synthesized peptides. Amino acid hydrolysates were prepared by treatment of samples in 6N hydrochloric acid, in vacuo, at 110° C. for 24 hours, followed by ion-exchange chromatography employing a Beckman System 6300 analyzer.

We routinely analyzed purity of the synthetic peptides by reverse-phase HPLC. Unless otherwise specified, peptide samples (20–100 μg) were applied to a Vydac $C_4$ column (0.46×25 cm) or an Aquapore RP-300 $C_8$ column (0.46×3.0 cm) using a Beckman Liquid Chromatographic System or an Applied Biosystems 150A Chromatographic System, respectively. The Vydac $C_4$ column was equilibrated in water containing 0.1% trifluoroacetic acid (TFA) and developed with a gradient of increasing acetonitrile concentration from 0 to 80% in the same TFA-containing solvent. The gradient was developed over 30 minutes at a flow rate of 1.0 ml/min. The effluent stream was monitored at 215 nm for absorbance. The Aquapore $C_8$ column was equilibrated in water containing 0.1% TFA and developed with an increasing gradient of acetonitrile concentration from 0 to 70% in a 0.085% TFA solvent. The gradient was developed for 45 minutes at a flow rate of 0.5 ml/min. The effluent stream was then monitored at 214 nm for absorbance.

EXAMPLE 1

Synthesis of Hirudin$_{53-64}$ and Hirudin$_{49-64}$

Hirudin$_{53-64}$ has the amino acid formula: H-Asn-Gly-Asp-Phe-Glu-Glu-Ile-Pro-Glu-Glu-Tyr-Leu-OH. Hirudin$_{49-64}$ has the amino acid formula: H-Glu-Ser-His-Asn-Asn-Gly-Asp-Phe-Glu-Glu-Ile-Pro-Glu-Glu-Tyr-Leu-OH. We prepared these peptides as part of a single synthesis by solid-phase peptide synthesis employing an Applied Biosystems 430 A Peptide Synthesizer (Applied Biosystems, Foster City, Calif.).

Specifically, we reacted 0.259 meq of Boc-Leu-O-resin (1% divinylbenzene resin (DVB)) sequentially with 2 mmoles of protected amino acids. Following 11 cycles of synthesis, 0.42 g of wet resin were removed from the reaction vessel. The remaining 0.43 g aliquot of wet resin was reacted with two times 2 mmoles of protected amino acids for four cycles. Hirudin$_{53-64}$ and hirudin$_{49-64}$ thus synthesized were fully deprotected and cleaved from the resin by treatment with anhydrous HF: p-cresol: ethyl methyl sulfate (10:1:1, v/v/v). Yield of the peptides was 56% and 53% for hirudin$_{49-64}$ and hirudin$_{53-64}$, respectively.

Individual HPLC analysis of the peptides revealed a high degree of purity and single predominant peaks of 214 nm-absorbing material eluting at 16.1 min and 16.3 min, respectively, for hirudin$_{49-64}$ and hirudin$_{53-64}$.

EXAMPLE 2

Synthesis Of des(Tyr-Leu)Hirudin$_{53-62}$

Des(Tyr-Leu) hirudin$_{53-62}$ has the amino acid formula: H-Asn-Gly-Asp-Phe-Glu-Glu-Ile-Pro-Glu-Glu-OH. We prepared des(Tyr-Leu) hirudin$_{53-62}$ as follows:

First, we prepared carboxypeptidase A, essentially as described by R. P. Ambler, "Enzymatic Hydrolysis with Carboxypeptidases", *Methods Enzymol.*, 25, part B, pp. 143-54. The enzyme (1.0 mg) was suspended in 1.0 ml of deionized water at 4° C. and centrifuged in a microfuge apparatus. We discarded the supernatant and added 100 µl of 1% sodium bicarbonate to the precipitate. We then added 0.1N NaOH dropwise, until the precipitate dissolved. The pH was then adjusted to 8.0 by the dropwise addition of 0.1N HCl. We adjusted the concentration of the enzyme to 1 mg/ml by the addition of 0.1M N-ethylmorpholine acetate, pH 8.25.

We dissolved 1.3 mg of hirudin$_{53-64}$, as prepared in Example 1, in 250 µl of 0.1M N-ethylmorpholine acetate, pH 8.25, containing 1.0M NaCl. We then added 30 µl (30 µg) of carboxypeptidase A as prepared above and incubated the reaction for 2 hours at 37° C.

Peptide fragments were purified by reverse phase HPLC employing an Aquapore RP-300 C$_8$ column (0.46×3.0 cm) and an Applied Biosystems 150 A liquid chromatographic system. The column was equilibrated in water containing 0.1% TFA and developed with a gradient of increasing acetonitrile concentration from 0 to 35% over 45 minutes at a flow rate of 0.5 ml/min in a 0.085% TFA-containing solvent. The effluent stream was monitored for absorbance at 214 nm. Fractions were collected manually, dried under vacuum and analyzed for amino acid composition and effects on clotting time of human plasma. We observed that des(Tyr-Leu) hirudin$_{53-62}$ elutes prior to any remaining intact hirudin$_{53-64}$.

EXAMPLE 3

Synthesis Of Hirudin$_{57-64}$

Hirudin$_{57-64}$ has the amino acid formula: H-Glu-Glu-Ile-Phe-Glu-Glu-Tyr-Leu-OH. To synthesize hirudin$_{57-64}$, we followed the procedure outlined in Example 1, except that we used 0.55 mmoles of Boc-Leu-OCH$_2$-PAM resin (1% DVB) (Applied Biosystems) in place of the Boc-Leu-O-resin (1% DVB). We then added 2 mmoles of protected amino acids at each cycle of coupling. The yield of crude peptide was 17.9%. HPLC analysis revealed a single predominant peak eluting at 14.2 min in the gradient.

EXAMPLE 4

Synthesis Of Hirudin$_{45-64}$

Hirudin$_{45-64}$ has the amino acid formula: H-Thr-Pro-Asn-Pro-Glu-Ser-His-Asn-Asn-Gly-Asp-Phe-Glu-Glu-Ile-Pro-Glu-Glu-Tyr-Leu-OH. We synthesized hirudin$_{45-64}$ using 0.259 meq of Boc-Leu-O-resin (1% DVB). We followed the procedure outlined in Example 1, except that we used 2 mmoles of protected amino acids in each coupling step for the first 13 cycles of synthesis. For the remaining 6 cycles of synthesis, we used two times 2 mmoles of protected amino acids. The peptide was fully deprotected and uncoupled from the DVB resin by treatment with anhydrous HF: p-cresol: ethyl methyl sulfate (10:1:1, v/v/v). Approximately 100 mg of peptide was recovered by extraction of the resin with 30% acetic acid. The yield of hirudin$_{45-64}$ was 17%.

A HPLC analysis revealed a high degree of purity (>90%) in the product and a single predominant peak of 214 nm absorbing material at 14.4 min in the acetonitrile gradient.

EXAMPLE 5

Synthesis Of Hirudin$_{55-64}$

Hirudin$_{55-64}$ has the amino acid formula: H-Asp-Phe-Glu-Glu-Ile-Pro-Glu-Glu-Tyr-Leu-OH. Hirudin$_{55-64}$ was prepared by the procedure outlined in Example 1, using 0.0259 meq of Boc-Leu-O-resin (1% DVB). We then added 2 mmoles of protected amino acids to the growing peptide at each cycle of coupling. Deprotection and cleavage from the resin was achieved as in the previous examples. The recovery of this peptide was 30%.

HPLC analysis revealed a high degree of purity (>95%) in the sample and a single predominant peak at 16.1 min in the acetonitrile gradient.

EXAMPLE 6

Synthesis Of Hirudin$_{64-45}$

Hirudin$_{64-45}$ has the amino acid formula: H-Leu-Tyr-Glu-Glu-Pro-Ile-Glu-Glu-Phe-Asp-Gly-Asn-Asn-His-Ser-Glu-Pro-Asn-Pro-Thr-OH. We synthesized hirudin$_{64-45}$ by the procedure outlined in Example 1, except that we used 0.259 meq of Boc-O-benzyl-L-Thr-O-resin (1% DVB) in place of the Boc-Leu-O-resin (1% DVB). We used 2 mmoles of protected amino acids in each coupling step for the first 6 cycles of synthesis. For the remaining cycles of synthesis, we used two times 2 mmoles of protected amino acids. The peptide was fully deprotected and uncoupled from the DVB resin by treatment with anhydrous HF. Following extraction with 30% acetic acid, 120 mg of peptide was recovered and the yield of hirudin$_{64-45}$ was 19.9%.

HPLC analysis of the peptide revealed a high degree of purity in the preparation (>90%) and a single predominant peak eluting at 13.7 min in the acetonitrile gradient.

We used hirudin$_{64-45}$ as a control in measuring the anticoagulant activities of various hirudin peptides [FIG. 2].

EXAMPLE 7

Synthesis Of Hirudin$_{54-64}$

Hirudin$_{54-64}$ has the amino acid formula: H-Gly-Asp-Phe-Glu-Glu-Ile-Pro-Glu-Glu-Tyr-Leu-OH. We synthesized hirudin$_{54-64}$ by the same procedure outlined in Example 1. We used 2 mmoles of protected amino acids in each coupling cycle of synthesis. After synthesis, the peptide was fully deprotected and uncoupled from the DVB resin as in the previous examples.

HPLC analysis revealed a high degree of purity (>60%) in the product and a single predominant peak of 214 nm absorbing material.

EXAMPLE 8

Further Purification Of Hirudin Peptides By HPLC

For the purpose of activity analysis, hirudin$_{45-64}$, hirudin$_{49-64}$ and hirudin$_{53-64}$, as prepared above, were purified to homogeneity by preparative reverse-phase HPLC employing a Waters Associates (Milford, Mass.) liquid chromatography system. Samples of the crude peptides (25 mg each of hirudin$_{45-64}$ and hirudin$_{49-64}$, 30 mg of hirudin$_{53-64}$) were dissolved in 2.0 ml of 0.1% TFA in water. An additional 1.0 ml of 6M guanidinium chloride was added to crude samples of hirudin$_{49-64}$ and hirudin$_{53-64}$ to increase solubility. The samples were separately injected on a Vydac C$_{18}$ column (22 mm×25 cm) previously equilibrated in 0.1% TFA in water. The column was developed with a linear gradient of increasing acetonitrile concentration from 0 to 80% over 45 minutes in the same TFA-containing solvent at a flow rate of 4.0 ml/min. The effluent stream was monitored at 229 nm and fractions collected manually.

Other hirudin peptides may be similarly prepared and purified.

EXAMPLE 9

Synthesis Of N-Acetyl Hirudin$_{53-64}$

N-acetylation of hirudin peptides was achieved directly during peptide synthesis. For example, N-acetyl hirudin$_{53-64}$ was synthesized by the basic procedure used to synthesize hirudin$_{53-64}$ described in Example 1. In order to carry out N-acetylation, however, we modified the procedure by substituting 2 mmoles of N-acetyl-asparagine for 2 mmoles of asparagine in the final cycle of peptide synthesis. Other hirudin peptides may be similarly N-acetylated by substituting the N-acetyl form of the amino terminal amino acid for the unacetylated form in the last cycle of peptide synthesis.

EXAMPLE 10

Sulfation Of Hirudin Peptides

Hirudin$_{53-64}$ was O-sulfated at the tyrosine residue to prepare Tyr$_{63}$-O-sulfate-hirudin$_{53-64}$, using the chemical modification procedure of T. Nakahara et al., "Preparation of Sulfated Tyrosine-O-[$^{35}$S] Sulfated Cholecystokinin Octapeptide from a Non-Sulfated Precursor Peptide", Anal. Biochem., 154, pp. 194-99 (1986). We dissolved 1.5 mg of hirudin$_{53-64}$, as prepared in Example 1, in 50 μl of dimethylformamide and dried the solution under N$_2$. The peptide was then redissolved in 40 μl of dimethylformamide (DMF) containing 2×10$^{-5}$ moles of sulfuric acid. To this we added 10 μl of a solution containing 50 μg N,N'-dicyclohexylcarbodiimide in 40 μl DMF (7.0×10$^{-5}$ moles). The reaction was allowed to proceed for about 5-10 min at 25° C. before adding 750 μl of deionized water. Any insoluble reaction products were removed by centrifugation in a microfuge apparatus prior to further purification.

Figure 1:
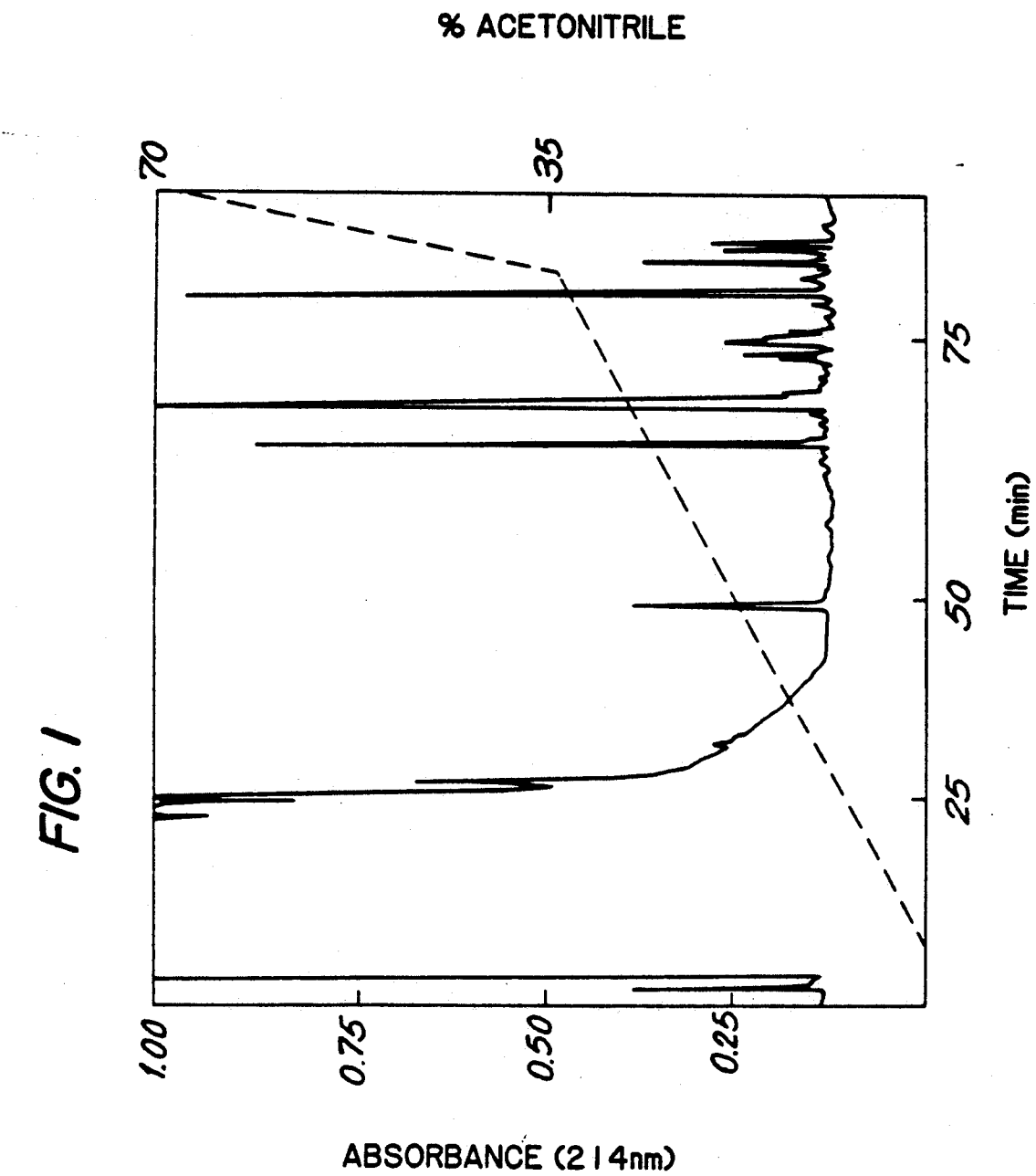
FIG. 1 depicts the purification of $Tyr_{63}$-O-sulfate hirudin$_{53-64}$ by reverse-phase HPLC.

Tyr$_{63}$-O-sulfate-hirudin$_{53-64}$ was purified away from other peptide and reaction components by reverse-phase HPLC employing a Vydac C$_{18}$ column (4.6×25 cm) and an Applied Biosystems, Inc., liquid chromatographic system. The column was equilibrated in a 0.1% TFA-water solvent and developed with a linear gradient of increasing acetonitrile concentration from 0 to 35% over 90 min at a flow rate of 0.8 ml/min with a 0.085% TFA-containing solvent. Fractions were collected, dried in a speed-vac apparatus and redissolved in deionized water. As shown in FIG. 1, a large number of peaks of 214 nm absorbing material were resolved.

By assaying the peak fractions for anti-coagulant activity, we identified two potential Tyr$_{63}$-O-sulfate-hirudin$_{53-64}$-containing fractions (peaks A and B; FIG. 1). Ultraviolet spectral analysis of peak A at neutral pH revealed a maximal absorbance at 258-264 nm, indicating the presence of a modified tyrosine residue. Amino acid analysis of the peptide in peak A confirmed the hirudin$_{53-64}$ structure. These data demonstrated that peak A contained Tyr$_{63}$-O-sulfate-hirudin$_{53-64}$.

We confirmed the presence of Tyr$_{63}$-O-sulfate-hirudin$_{53-64}$ by treating the peptide of peak A with 30% TFA at 60° C. for 1 hour to remove the sulfate group. We then dried the peptide, redissolved it in water and subjected it to reverse-phase HPLC. We carried out HPLC analysis of the desulfated Tyr$_{63}$-O-sulfate-hirudin$_{53-64}$ using an Aquapore RP-300 C$_8$ column (0.46×3.0 cm) and an Applied Biosystems 150A HPLC system. The column was equilibrated in water containing 0.1% TFA and developed with a gradient of increasing acetonitrile concentration from 0 to 70% over 45 minutes at a flow rate of 0.5 ml/min in a 0.085% TFA-containing solvent. The peptide showed HPLC chromatographic behavior identical to that of unsulfated hirudin$_{53-64}$. In addition, peak absorbance of the treated peptide returned to 275-280 nm, typical for a peptide containing an unmodified tyrosine residue.

We then applied the above-described sulfation procedure to large quantities of the corresponding N-acetylated peptide. Treatment of 25 mg of N-acetyl-hirudin$_{53-64}$ (as prepared in Example 9) by the Nakahara procedure produced an 80.1% yield of the desired Tyr-sulfated product. However, efforts to scale the reaction proportionally to 50 mg of N-acetyl-hirudin$_{53-64}$ only resulted in a 48.5% yield of the Tyr-sulfated derivative.

Accordingly, we significantly modified the chemistry of the Nakahara procedure to achieve a high yield of the Tyr-sulfated derivative in a large scale sulfation reaction. More specifically, we dissolved 1 g of N-acetyl-hirudin$_{53-64}$ in 40 ml of dimethylformamide in the presence of 5.0 ml of N,N'-dicyclohexylcarbodiimide (0.2 g/0.16 ml dimethyl formamide). The mixture was stirred at 0° C. and 0.5 ml of concentrated sulfuric acid was added dropwise to the reaction mixture until a precipitate formed. Following 5 minutes, the reaction was stopped by the addition of 40 ml water. Reverse-phase HPLC separation of the reaction mixture indicated a 81.7% yield of the sulfated peptide, $Tyr_{63}$O-sulfate-N-acetyl-hirudin$_{53-64}$.

Large-scale purification of the sulfated hirudin peptide was then achieved by a one-step anion exchange chromatography. Specifically, crude $Tyr_{63}$O-sulfate-N-acetyl-hirudin$_{53-64}$ was purified on a column of DEAE-Sepharose (250 ml wet resin/5 g crude peptide). The column was pre-equilibrated and the sample was loaded in 20 mM sodium acetate, pH 5.0. The column was developed with a linear NaCl gradient (0–0.4M). The $Tyr_{63}$O-sulfate-N-acetyl-hirudin$_{53-64}$ eluted at approximately 0.2–0.3M NaCl, after the unsulfated peptide, but prior to the sulfonated side product 3-Sulfo-$Tyr_{63}$-acetyl-hirudin$_{53-64}$.

Other hirudin peptides may be sulfated, purified and analyzed by procedures identical to those set forth above.

EXAMPLE 11

Sulfonation Of Hirudin Peptides

N-acetyl-hirudin$_{53-64}$ was modified to its Tyr-sulfonated derivative, 3-Sulfo-$Tyr_{63}$-N-acetyl-hirudin$_{53-64}$, during the preparation of $Tyr_{63}$-O-sulfate-N-acetyl-hirudin$_{53-64}$, as described in Example 10. 3-Sulfo-$Tyr_{63}$-N-acetyl-hirudin$_{53-64}$ was a side reaction product obtained duiing the large-scale sulfation reaction described in that example. Accordingly, 3-Sulfo-$Tyr_{63}$-N-acetyl-hirudin$_{53-64}$ was obtained at between 30 to 40% yield and was found to elute prior to $Tyr_{63}$-O-sulfate hirudin$_{53-64}$ in reverse-phase HPLC separations. Hirudin$_{53-64}$ was similarly modified to its Tyr-sulfonated derivative. Other hirudin peptides may also be sulfonated by a similar procedure.

EXAMPLE 12

Preparation Of A Polyethyleneglycol Conjugate Of $Tyr_{63}$-O-sulfate Hirudin$_{53-64}$ We coupled a hirudin peptide to a pharmaceutically acceptable polymer in order to increase the half-life of the peptide. More specifically, we prepared a derivative of polyethyleneglycol, polyethyleneglycol N-succinimidyl succinate (SS-PEG; avg. MW=5,000), by conventional methods [Abuchowski et al., *Cancer Biochem. Biophys.*, 7, pp. 175–86 (1984)]. We then dissolved 100 μof $Tyr_{63}$-O-sulfate-hirudin$_{53-64}$, as prepared in Example 10, in 200 μl of 20 mM sodium borate, pH 9.0 and reacted it with a 50-fold molar excess of SS-PEG. The reaction was let stand at room temperature overnight and then applied to reverse phase HPLC for purification and characterization.

Reverse-phase HPLC was performed using an Aquapore RP-300 $C_8$ column (0.46×3.0 cm) using an Applied Biosystems 150A chromatographic system. The column was equilibrated in water containing 0.1% TFA and developed with an increasing gradient of acteonitrile from 0 to 50% in a 0.085% TFA solvent over 45 minutes at a flow rate of 0.5 ml/min. The effluent stream was monitored at 214 nm for absorbance. We observed that the SS-PEG derivative of $Tyr_{63}$-O-sulfate-hirudin$_{53-64}$ elutes earlier than the underivatized form and is contained within a broader peak. Comparison of the anticoagulant activity of both the derivatized and underivatized forms of $Tyr_{63}$-O-sulfate-hirudin$_{53-64}$ revealed identical dose-dependencies for increase in APTT. Thus, the SS-PEG-$Tyr_{63}$-O-sulfate-hirudin$_{53-64}$ is an active derivative of a hirudin peptide that advantageously exhibits an expected increase in circulating half-life when compared to its underivatized counterpart.

EXAMPLE 13

Peptidomimetic Analogs

Hirudin peptides, preferably, $Tyr_{63}$-O-sulfate-hirudin$_{53-64}$, may be used to produce semi-peptidic or non-peptidic peptidomimetic analogs, synthetic molecules which exhibit anticoagulant and antiplatelet activities. Like hirudin peptides, these peptidomimetic analogs are characterized by inhibitory activity toward platelet aggregation.

The peptidomimetic analogs of hirudin peptides, hereinafter referred to as "hirulogs", are represented by the following chemical structures:

Hirulog-1:

```
Asp—Phe—Glu—Glu—Ile—Pro—Glu—Glu
  \                              \
   Gly                          Tyr(OSO3−H+)
    \                           /
     Asn—Cys—S—S—Cys—Leu
```

Hirulog-2:

```
Asp—Phe—Glu—Glu—Ile—Pro—Glu—Glu
  \                              \
   Gly                          Tyr(OSO3−H+)
    /                           /
   Asn—Cys—S—S—(CH2)n̄—S—S—Cys—Leu
```

Hirulog-3:

```
Asp—Phe—Glu—Glu—Ile—Pro—Glu—Glu
  \                              \
   Gly                          Tyr(OSO3−H+)
    /                           /
   Asn—Cys—S—CH—(CH2)n̄—CH—S—Cys—Leu
              |              |
             COOH           COOH
```

Hirulog-4:

```
Asp—Phe—Glu—Glu—Ile—Pro—Glu—Glu
  \                              \
   Gly     H         O          Tyr(OSO3−H+)
    /      |         ||         /
   Asn—Lys—N—C—(CH2)n̄—C—N—Lys—Leu
              ||            H
              O
```

Hirulog-5:

```
Asn—Gly—Asp—Phe—Glu—Glu—Ala
                       /    \
                      O     Pro
                      |      |
                      C=O   Glu
                       \    /
                  Leu—(OSO3−H+)Tyr—Glu
```

Hirulog-6:

```
Asn—Gly—Asp—Phe—Glu—Glu—Ala—Pro
                       |     |
                       O     Glu
                        \   /
                Leu—(OSO3−H+)Tyr—Ser
```

Hirulog-7:

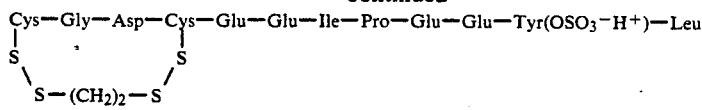

Semi-peptidic peptidomimetic analogs of hirudin peptides may be prepared to stabilize a loop, turn, or helical conformation of the parent peptide. For example, a loop structure is constructed by the addition of cysteinyl or lysyl residues at both the N- and C-terminal ends of $Tyr_{63}$-O-sulfate hirudin$_{53-64}$. Terminal cysteinic residues are crosslinked by oxidation to produce Hirulog-1 (FIG. 3A), oxidation with an aliphatic dithiol to produce Hirulog-2 (FIG. 3B), or alkylation with aliphatic dihaloacetate or propionate to produce Hirulog-3 (FIG. 3C). Terminal lysyl residues are crosslinked with any of a number of imidate agents which vary in spacer length or with dihydroxysuccinimidyl aliphatic reagents, resulting in production of Hirulog-4 (FIG. 4A).

A turn structure around Pro-8 of $Tyr_{63}$-O-sulfate-hirudin$_{53-64}$ is constrained by replacement of Ile-7 with chloroalanine, with or without concomitant replacement of Glu-9 or Glu-10 with (L) or (D)-serine. Peptidomimetic analogs containing chloroalanine alone would yield cross-linking of Glu-9 or Glu-10 to Ala-7 with a ketone linkage to produce Hirulog-5 (FIG. 5A). Derivatives with serine at positions 9 or 10 would yield crosslinking via an ether linkage, producing Hirulog-6 (FIG. 5B).

A helical structure in the peptidomimetic analogs can be constrained by substituting cysteinyl residues at position (n) and (n+3) of the hirudin peptide and crosslinking by either direct oxidation, oxidation with an aliphatic dithiol, or alkylation with an aliphatic dihalo acetate. For example, replacement of Asn-1 and Phe-4 of $Tyr_{63}$-O-sulfate-hirudin$_{53-64}$ with cysteines and oxidation via ethanedithiol (FIG. 6) would constrain a helical turn in the NH$_2$-terminal side of the derivative and, thus, seed a stable helical structure in the peptide derivative. This is exemplified by Hirulog-7.

Fully non-peptidic peptidomimetic analogs may also be produced taking into account the above-described strategies relating to constrained peptide compounds.

EXAMPLE 14

Preparation Of Platelet-Rich And Platelet-Poor Plasma

We prepared platelet-rich and platelet-poor plasma, according to the method of J. A. Jakubowski and N. G. Ardlie, "Modification of Human Platelet Function By A Diet Enriched in Saturated or Polyunsaturated Fat", *Atherosclerosis*, 31, pp. 335-44 (1978). Specifically, we collected blood from healthy human volunteers via a 21 gauge butterfly cannula into a 1/10 final volume of 3.8% trisodium citrate. All donors had avoided the use of medication of any kind for at least 2 weeks prior to blood collection. Platelet-rich plasma was prepared by room temperature centrifugation of the citrated whole blood for 15 minutes at 100× g in a Sorval rotor. We prepared platelet-poor plasma by centrifuging the citrated whole blood for 15 minutes at 12,000× g.

EXAMPLE 15

Antiplatelet Activity Of $Tyr_{63}$-O-sulfate Hirudin$_{53-64}$

We analyzed the effect of hirudin$_{53-64}$ or $Tyr_{63}$-O-sulfate hirudin$_{53-64}$ on the inhibition of platelet aggregation caused by various concentrations of thrombin. Specifically, varying amounts of hirudin$_{53-64}$ or Sulfo- hirudin$_{53-64}$, contained in 0.05 ml water, were added to 0.4 ml of prewarmed (37° C.) platelet-rich plasma prepared according to Example 14, to a final concentration of 0-11 $\mu$/ml final assay volume. The peptide/platelet mixture was incubated for 1 minute at 37° C. We then added 0.05 ml of human $\alpha$-thrombin (a gift of Dr. J. Fenton II; New York Department of Health), to a final concentration of either 0.20, 0.25 or 0.5 U/ml total assay volume. These concentrations of $\alpha$-thrombin are believed to equal the levels achieved in vivo and which allow platelet aggregation studies to be performed in plasma without a major interference of clot formation.

We monitored the extent of platelet aggregation turbidimetrically for 4 minutes using a Biodata 4-Channel Platelet Aggregation Profiler (PAP-4; Biodata Corp., Hatboro, Pa.). Platelet aggregation was terminated by the addition of ice-cold indomethacin added to a final concentration of 10 %. The maximum platelet aggregation observed during the 4 minutes was plotted against the concentration of hirudin$_{53-64}$ or Sulfo- present in the assay mixture.

FIG. 7 demonstrates the effect of Sulfo-Tyr6-%hirudin$_{53-64}$ on the maximal extent of platelet aggregation induced by 0.25 and %.5 U/ml $\alpha$-thrombin. As illustrated in that figure, Sulfo-Tyr63hirudin$_{53-64}$ inhibited the ability of thrombin to aggregate human platelets in a dose-dependent manner. FIG. 7 also demonstrates that when platelet aggregation was induced by the higher concentration of $\alpha$-thrombin, a correspondingly higher concentration of Sulfo-Tyr63hirudin$_{53-64}$ was required to inhibit the aggregation response. The IC50 (the concentration of - Sulfo- hirudin$_{53-64}$ required to decrease platelet aggregation to 50% of maximum) for 0.25 U/ml of $\alpha$-thrombin was 0.72 $\mu$/ml and for 0.5 U/ml of $\alpha$-thrombin it was 2.2 $\mu$/ml. FIG. 8 demonstrates that hirudin$_{53-64}$ also inhibits thrombin-induced platelet aggregation in a dose-dependent manner, but is approximately 30-fold less potent than $Tyr_{63}$-O-sulfate-hirudin$_{53-64}$.

We further assessed the effects of $Tyr_{63}$-O-sulfate-hirudin$_{53-64}$ on thrombin-induced platelet activities by assaying serotonin release and thromboxane A$_2$ generation. The serotonin release assy, was performed as follows. The platelets in approximately 20 ml of platelet-rich plasma, prepared as described in Example 14, were loaded with $^{14}$C-serotonin by incubating the plasma with 27 nCi/ml of 5-[2-$^{14}$C]serotonin binoxalate (60 mCi/mmole; DuPont-New England Nuclear, Boston, Mass.) at 37° C. for 30 minutes. Under these conditions, platelets incorporated 90.1±1.3% (mean+SD, n=6) of the added serotonin, resulting in a specific activity of approximately 10,000 counts/minute/ml of platelet-rich plasma.

We mixed 0.4 ml of the platelet-rich plasma containing $^{14}$C-serotonin loaded platelets in the aggregometer with varying concentrations (0-11 $\mu$/ml total assay volume) of $Tyr_{63}$-O-sulfate-hirudin$_{53-64}$ contained in 0.05 ml saline for 1 minute at 37° C. We then added 0.05 ml of human $\alpha$-thrombin, to a final concentration of either 0.25 or 0.5 U/ml of the total assay volume and incubated at 37° C. for 4 more minutes. The thrombin-induced serotonin release reaction was stopped and reuptake by the platelets was halted by the addition of a 1/10th volume of an ice-cold cocktail containing 3.3% EDTA, 10 mM theophylline, 1 μ/ml prostaglandin $E_1$, and 500 μM imipramine (hereinafter "ETPI"). The first three components are commonly used to prevent the platelet release reaction [J. A. Jakubowski and N. G. Ardlie, "Further Observations on the Effects of Dietary Fatty Acid Composition on Platelet Reactivity and Blood Coagulation in Man and the Influence of Methodology on Findings", *Atherosclerosis,* 41, pp. 285–94 (1982)]. Imipramine is a serotonin receptor agonist which prevents reuptake during sample handling. We have determined that EPTI inhibited serotonin uptake and release by >95%.

Following the addition of EPTI to the platelet samples, the platelets were removed by centrifugation at 12,000× g for 2 minutes in a Sorval rotor. Serotonin release was assayed by measuring $^{14}C$-radioactivity in the supernatant using liquid scintillation counting (Tri-Carb 1500; Packard Instruments). FIG. 9 shows that $Tyr_{63}$-O-sulfate-hirudin 3–64 inhibited serotonin release in a dose-dependent manner, similar to that observed for inhibition of platelet aggregation (see FIG. 7).

Platelets contained in platelet-rich plasma were stimulated with thrombin in the presence of increasing concentrations of $Tyr_{63}$-O-sulfate hirudin$_{53-64}$ (0–11 μg/ml). The assay was performed as described above. Specifically, varying concentrations of $Tyr_{63}$-O-sulfate-hirudin$_{53-64}$ in 0.5 ml saline were added to 0.4 ml of platelet-rich plasma and the mixture was incubated for 1 minute at 37° C. We then added α-thrombin contained in 0.05 ml saline to a final concentration of either 0.5 or 0.25 U/ml and incubated the mixtures for 4 minutes at 37° C. Platelet thromboxane $A_2$ generation was quenched by the addition of ice-cold indomethacin to a final concentration of 10 μM, followed by centrifugation at 12,000× g for 2 minutes. The supernatant plasma was stored at −20° C. prior to assaying for thromboxane $A_2$ content. Thromboxane $A_2$ was assayed by a radioimmunoassay that detects thromboxane $B_2$, a stable hydrolytic product and indicator of thromboxane $A_2$ [J. A. Jakubowski et al., "Cumulative Antiplatelet Effect of Low-Dose Enteric Coated Aspirin", *Br. J. Haematol.,* 60, pp. 635–42 (1985)].

FIG. 10 demonstrates that $Tyr_{63}$-O-sulfate-hirudin$_{53-64}$ inhibits thrombin-induced thromboxane $A_2$ generation in platelets in a dose-dependent manner, similar to that previously observed for inhibition of platelet aggregation and serotonin release. 3-Sulfo-$Tyr_{63}$-hirudin$_{53-64}$ demonstrates platelet inhibitory activity which parallels that of $Tyr_{63}$-O-sulfate-hirudin$_{53-64}$.

EXAMPLE 16

Activity $Tyr_{63}$-O-sulfate-hirudin$_{53-64}$ On Heparin-Induced Thrombocytopenic Blood We carried out various in vitro assays to illustrate the efficacy of $Tyr_{63}$-O-sulfate hirudin$_{53-64}$ in the treatment of patients suffering from heparin-induced thrombocytopenia.

The platelet-rich plasma used in these assays was obtained from patients after cessation of heparin therapy and recovery from heparin-induced thrombocytopenia.

We incubated platelet-rich plasma, obtained from various patients and prepared as in Example 14, with varying concentrations of porcine lung sodium heparin (0.05–0.5 U/ml; Elkins-Sinn, Cherry Hill, N.J.) or $Tyr_{63}$-O-sulfate-hirudin$_{53-64}$ (0.8–55 μg/ml). Platelet aggregation was monitored turbidometrically, as in Example 15. FIG. 11A demonstrates that heparin induced aggregation of patient platelets after the patient had fully recovered from heparin-induced thrombocytopenia. $Tyr_{63}$-O-sulfate-hirudin$_{53-64}$ did not induce platelet aggregation over the entire concentration range (FIG 11B).

Next, we determined the extent of thromboxane $A_2$ generation from similar platelets incubated with either heparin or $Tyr_{63}$-O-sulfate-hirudin$_{53-64}$. Platelet-rich plasma from patients who had recovered from heparin-induced thrombocytopenia was incubated with either heparin or $Tyr_{63}$-O-sulfate-hirudin$_{53-64}$ (1.7–55 μg/ml). Thromboxane $A_2$ secretion was stopped by the addition of indomethacin, followed by centrifugation and determined by assaying for thromboxane $B_2$, as in Example 15. The data presented below confirms that heparin causes platelet aggregation and release in patients with heparin-induced thrombocytopenia, while $Tyr_{63}$-O-sulfate-hirudin$_{53-64}$ does not.

| Agent | Thromboxane $A_2$ (ng/$10^8$ platelets) |
|---|---|
| heparin (0.05 U/ml) | 36 |
| heparin (0.5 U/ml) | 123 |
| Tyr—O-sulfate hirudin$_{53-64}$ (1.7 μg/ml) | <1 |
| Tyr—O-sulfate hirudin$_{53-64}$ (7 μg/ml) | <1 |
| Tyr—O-sulfate hirudin$_{53-64}$ (55 μg/ml) | <1 |

We next confirmed that the concentrations of both heparin and $Tyr_{63}$-O-sulfate-hirudin$_{53-64}$ used in the above assay were sufficient to cause an increase in activated partial thrombin time (APTT). We isolated whole blood from patients who had recovered from heparin-induced thrombocytopenia. We then centrifuged the blood at 4° C. for 15 minutes at 2,000× g in a Sorval rotor to obtain plasma. We then added 0.05 ml of either heparin or $Tyr_{63}$-O-sulfate-hirudin$_{53-64}$ to 0.1 ml of plasma, approximately 2 minutes prior to activation by the addition of 0.1 ml of 0.3M $CaCl_2$ and then, 100 μl of a platelet factor 3 reagent (General Diagnostics Organon Teknika, Durham, N.C.). We measured APTT semi-automatically using a Coagamate XC (General Diagnostics Organon Teknika). FIGS. 12A and 12B confirm that the concentrations of heparin and $Tyr_{63}$-O-sulfate-hirudin$_{53-64}$ used in the platelet studies were sufficient to prolong APTT into the desired therapeutic range.

These assays illustrate that in the platelet-rich plasma of patients with heparin-induced thrombocytopenia, doses of heparin required to achieve anticoagulant effects lead to platelet activation and, thus, an increased risk of thrombosis. In sharp contrast, we have demonstrated the surprising and unexpected result that hirudin peptides, preferably $Tyr_{63}$-O-sulfate-hirudin$_{53-64}$ anticoagulate plasma without causing activa in patients afflicted with this autoimmune disorder. Therefore, in patients with heparin-induced thrombocytopenia, hirudin peptides and compositions containing them constitute a safe and effective alternative to heparin as anticoagulant agents and agents which inhibit platelet aggregation.

While we have hereinbefore presented a number of embodiments of this invention, it is apparent that our basic construction can be altered to provide other embodiments which utilize the processes and products of this invention. Therefore, it will be appreciated that th scope of this invention is to be defined by the claims appended hereto rather than the specific embodiments which have been presented hereinbefore by way of example.

We claim:

1. A method for inhibiting platelet aggregation in stored platelets comprisnig the step of storing platelets in the presence of a composition comprising:
   (a) a pharmaceutically effective amount of a peptide sufficient to inhibit platelet aggregation in stored platelets, said peptide consisting of the formula: Y-Phe-Glu-Glu-Ile-Pro-Glu-Glu-Tyr-Z, or D-retro forms of said peptide; wherein Y is selected from the group consisting of H, an amino protecting group, Asp, any sequential portion of the amino acid sequence: Val-Thr-Gly-Glu-Gly-Thr-Pro-Lys-Pro-Gln-Ser-His-Asn-Asp-Gly-Asp, said sequential portion comprising at least two C-terminal amino acids of said amino acid sequence; and any sequential portion of the amino acid sequence: Val-Thr-Gly-Glu-Gly-Thr-Pro-Asn-Pro-Glu-Ser-His-Asn-Asn-Gly-Asp, said sequential portion comprising at least two C-terminal amino acids of said amino acid sequence; Z is selected from the group consisting of OH, Leu and Leu-Gln; and the tyrosine residue contains a negatively charged side group; and
   (b) a pharmaceutically acceptable carrier.

2. The method according to claim 1, wherein the pharmaceutically effective amount of said peptide of part (a) is between about 0.5 µg/ml and about 1,000 µg/ml.

3. The method according to claim 2, wherein the pharmaceutically effective amount of said peptide is between about 5 µg/ml and about 100 µg/ml.

4. A method of inhibiting platelet aggregation in a patient, said method comprising the step of treating said patient in a pharmaceutically accpetable manner with a composition comprisign: (a) a pharmaceutically effective amount of a peptide sufficient to inhibit platelet aggregation in a patient, said peptide consisting of the formula: Y-Phe-Glu-Glu-Ile-Pro-Glu-Glu-Tyr-Z, or D-retro forms of said peptide; wherein Y is selected from the group consisting of H, an amino protecting group, Asp, any sequential portion of the amino acid sequence: Val-Thr-Gly-Glu-Gly-Thr-Pro-Lys-Pro-Gln-Ser-His-Asn-Asp-Gly-Asp, said sequential portion comprising at least two C-terminal amino acids of said amino acid sequence; and any sequential portion of the amino acid sequence: Val-Thr-Gly-Glu-Gly-Thr-Pro-Asn-Pro-Glu-Ser-His-Asn-Asn-Gly-Asp, said sequential portion comprising at least two C-terminal amino acids of said amino acid sequence; Z is selected from the group consisting of OH, Leu and Leu-Gln; and the tyrosine residue contains a negatively charged side group; and
   (b) a pharmaceutically acceptabl carrier.

5. The method according to calim 4, wherein said pharmaceutically effective amount of peptide of part (a) is between about 0.1 mg/kg body weight and about 10 mg/kg body weight.

6. The method according to calim 5, wherein said pharmaceutically effective amount of peptide is betwen about 0.2 mg/kg body weight and about 2 mg/kg body weight.

7. The method according to calim 4, wherein at the time of treatment, said patient is suffering from or has suffered from heparin-induced thrombocytopenia.

8. The method according to calim 4, wherien said patient is a human.

9. A method for inhibiting platelet aggreation in stored platelets comprisnig the step of storing platelets in the presence of a compostiion comprising a pharmaceutically effective amount of at least one peptide selected from the group consisting of:
   (a) peptides characterized by a sequence of amino acids consisting of the formula:

Asn-Gly-Asp-Phe-Glu-Glu-Ile-Pro-Glu-Glu-Tyr-X;

and
   (b) D-retro forms of the peptides of (a); wherein X is selected from the group consisting of OH, Leu and Leu-Gln.

10. A method for inhibiting platelet aggregation in a patient comprising the step of treating said patient in a pharmaceutically accpetable manner with a composition comprisign a pharmaceutically acceptable carrier and a pharmaceutically effective amount of at least one peptide selected from the group consisting of:
   (a) peptides characterized by a sequence of amino acids consisting of the fomrula:

Asn-Gly-Asp-Phe-Glu-Glu-Ile-Pro-Glu-Glu-Tyr-X;

and
   (b) D-retro forms of the peptides of (a); wherein X is selected from the group consisting of OH, Leu and Leu-Gln.

11. The method according to calim 10, wherein at the time of treatment, said pateint is suffereing from heparin-induced thrombocytopenia.

12. The method according to calim 10, wherein at the time of treatment, said pateint has suffered from heparin-induced thrombocytopenia.

13. The method according to claim 10 or 11, wherein said patient is a human.

14. The method according to any one of claims 1, 4, 7 or 8, wherien said peptide of (a) is selected from the group consisting of $Tyr_{63}$-O-sulfate-hirudin 3–64 and 3-sulfo-$Tyr_{63}$-hirudin$_{53-64}$.

15. The method according to claim 1, wherien said composition additionally comprises a pharmaceutically effective amount of a compound sufficient to inhibit platelet aggregation in stored platelets, said compound being selected from the group consisting of metal chelaters, prostaglandins, theophylline, small peptide platelet inhibitors, inhibitors of platelet surface components, antibodies against platelet surface components, analogs thereof which display antiplatelet activity and combinations thereof.

16. The method according to calim 4, wherein said composition additionally comprises a pharmaceutically effective amount of a compuond sufficient to inhibit platelet aggregation in a patient, said compuond being selected from the group consisting of cyclooxygenase inhibitors, small non-peptide platelet inhibitors, prostaglandins, theophylline, small peptide platelet inhibitors, hematopoietic factors, inhibitors of platelet surface components, antibodies against platelet surface components, analogs thereof whcih display antiplatelet activity and combinations thereof.

* * * * *